United States Patent
Blouin et al.

(10) Patent No.: US 9,048,433 B2
(45) Date of Patent: Jun. 2, 2015

(54) CONJUGATED POLYMERS

(75) Inventors: Nicolas Blouin, Southampton (GB); Steven Tierney, Southampton (GB); William Mitchell, Chandler's Ford (GB); Miguel Carrasco-Orozco, Winchester (GB)

(73) Assignee: MERCK PATENT GMBH, Darmstadt (DE)

( * ) Notice: Subject to any disclaimer, the term of this patent is extended or adjusted under 35 U.S.C. 154(b) by 183 days.

(21) Appl. No.: 13/993,693

(22) PCT Filed: Nov. 17, 2011

(86) PCT No.: PCT/EP2011/005806
§ 371 (c)(1),
(2), (4) Date: Jun. 13, 2013

(87) PCT Pub. No.: WO2012/079675
PCT Pub. Date: Jun. 21, 2012

(65) Prior Publication Data
US 2013/0256604 A1    Oct. 3, 2013

Related U.S. Application Data

(60) Provisional application No. 61/424,174, filed on Dec. 17, 2010.

(30) Foreign Application Priority Data

Dec. 17, 2010   (EP) .................................. 10015798

(51) Int. Cl.
| | | |
|---|---|---|
| H01B 1/12 | (2006.01) | |
| C08G 75/00 | (2006.01) | |
| H01L 51/00 | (2006.01) | |
| C07D 495/04 | (2006.01) | |
| C08G 61/12 | (2006.01) | |
| C08L 65/00 | (2006.01) | |
| H01L 51/05 | (2006.01) | |

(52) U.S. Cl.
CPC .......... *H01L 51/0043* (2013.01); *C07D 495/04* (2013.01); *C08G 61/123* (2013.01); *C08G 2261/124* (2013.01); *C08G 2261/1412* (2013.01); *C08G 2261/3223* (2013.01); *C08G 2261/3243* (2013.01); *C08G 2261/344* (2013.01); *C08G 2261/414* (2013.01); *C08G 2261/51* (2013.01); *C08G 2261/91* (2013.01); *C08G 2261/92* (2013.01); *C08G 2261/95* (2013.01); *C08L 65/00* (2013.01); *H01B 1/127* (2013.01); *H01L 51/0036* (2013.01); *H01L 51/0053* (2013.01); *H01L 51/0545* (2013.01); *Y02E 10/549* (2013.01)

(58) Field of Classification Search
CPC ..................... H01L 51/0043; C08G 2261/124; C08G 2261/1412; C08G 2261/3223; C08G 2261/344; C08G 2261/414; C08G 2261/51; C08G 2261/91; C08G 2261/92; C08G 2261/95
USPC ................. 528/370, 373, 377, 378, 380, 425; 252/500
See application file for complete search history.

(56) References Cited

U.S. PATENT DOCUMENTS

| 8,334,456 B2 | 12/2012 | Zhu et al. | |
|---|---|---|---|
| 8,431,680 B2 * | 4/2013 | Mishra et al. | ................. 528/380 |
| 2010/0307594 A1 | 12/2010 | Zhu et al. | |
| 2012/0187385 A1 | 7/2012 | Pan et al. | |
| 2013/0098448 A1 | 4/2013 | Zhu et al. | |

FOREIGN PATENT DOCUMENTS

| DE | 3917323 | * | 11/1990 |
|---|---|---|---|
| JP | 4338761 A | | 11/1992 |
| WO | 2007003520 A1 | | 1/2007 |
| WO | 2010135701 A1 | | 11/2010 |

OTHER PUBLICATIONS

Lorenze Testaferri, Marcello Tiecco, Paolo Zanirato, Giorgio Martelli. "Preparation and Tautomeric Structures of some Potential 2,5-Dihydroxythieno[3,2-b]thiophenes" J. Org. Chem., vol. 43, No. 11, p. 2197-2200, 1978.*
International Search Report from PCT/EP2011/005806 dated Jun. 13, 2012.
Erhard Gunther et al. "2,5-Bis(cyanimino)-2,5-dihydrothieno[3,2-b]thiophenes—A New Acceptor Type: Synthesis and General Properties" Chem. Ber. [1992] 125, pp. 1235-1241.
Kai Zhang et al. "Highly Luminescent Polymers Containing the 2,3,5,6-Tetraarylated Pyrrolo[3,4-c]pyrrole-1,4-dione (N-Aryl DPP) Chromophore in the Main Chain" Macromolecules [2008] 41, pp. 7287-7295.

* cited by examiner

*Primary Examiner* — Peter F Godenschwager
*Assistant Examiner* — Andrew J Oyer
(74) *Attorney, Agent, or Firm* — Millen, White, Zelano, Branigan, P.C.

(57) ABSTRACT

The invention relates to novel polymers containing one or more thieno[3,2-b]thiophene-2,5-dione and/or furo[3,2-b]furan-2,5-dionerepeating units or their thioketone derivatives, monomers and methods for their preparation, their use as semiconductors in organic electronic (OE) devices, especially in organic photovoltaic (OPV) devices, and to OE and OPV devices comprising these polymers.

30 Claims, 1 Drawing Sheet

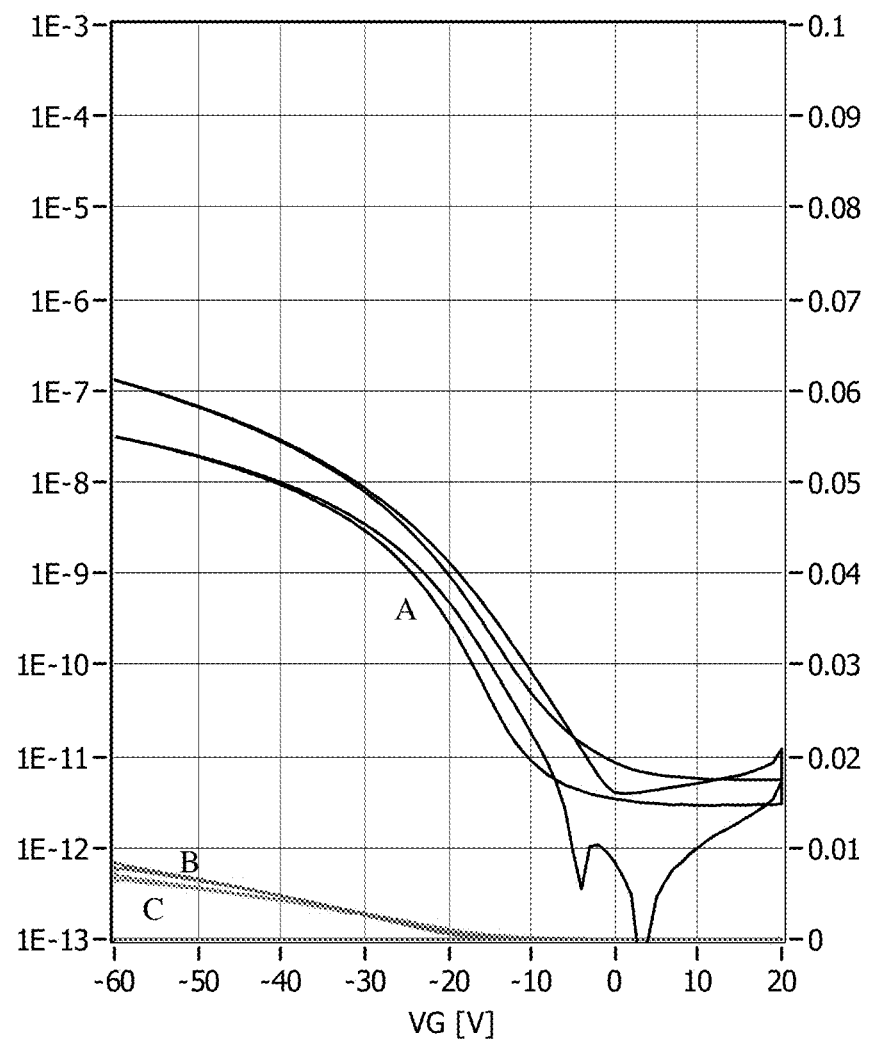

CONJUGATED POLYMERS

FIELD OF THE INVENTION

The invention relates to novel polymers containing one or more thieno[3,2-b]thiophene-2,5-dione and/or furo[3,2-b]furan-2,5-dione repeating units or their thioketone derivatives, monomers and methods for their preparation, their use as semiconductors in organic electronic (OE) devices, especially in organic photovoltaic (OPV) devices, and to OE and OPV devices comprising these polymers.

BACKGROUND OF THE INVENTION

In recent years there has been growing interest in the use of conjugated, semiconducting polymers for electronic applications. One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies up to 8%.

The conjugated polymer serves as the main absorber of the solar energy, therefore a low band gap is a basic requirement of the ideal polymer design to absorb the maximum of the solar spectrum. A commonly used strategy to provide conjugated polymers with narrow band gap is to utilize alternating copolymers consisting of both electron rich donor units and electron deficient acceptor units within the polymer backbone.

However, the conjugated polymers that have been suggested in prior art for use ion OPV devices do still suffer from certain drawbacks. For example many polymers suffer from limited solubility in commonly used organic solvents, which can inhibit their suitability for device manufacturing methods based on solution processing, or suffer from open circuit potentials ($V_{oc}$) in OPV bulk-hetero-junction devices, or have only limited charge carrier mobility, or are difficult to synthesize by methods which are unsuitable for mass production.

Therefore, there is still a need for organic semiconducting (OSC) materials that are easy to synthesize, especially by methods suitable for mass production, show good structural organization and film-forming properties, exhibit good electronic properties, especially a high charge carrier mobility, good processibility, especially a high solubility in organic solvents, and high stability in air. Especially for use in OPV cells, there is a need for OSC materials having a low bandgap, which enable improved light harvesting by the photoactive layer and can lead to higher cell efficiencies, and do not suffer from open circuit potentials ($V_{oc}$) in OPV bulk-hetero-junction devices, or do so to a lower extent than polymers from prior art.

It was an aim of the present invention to provide compounds for use as organic semiconducting materials that do not have the drawbacks of prior art materials as described above, are easy to synthesize, especially by methods suitable for mass production, and do especially show good processibility, high stability, good solubility in organic solvents, high charge carrier mobility, and a low bandgap. Another aim of the invention was to extend the pool of OSC materials available to the expert. Other aims of the present invention are immediately evident to the expert from the following detailed description.

The inventors of the present invention have found that these aims can be achieved by providing conjugated polymers containing thieno[3,2-b]thiophene-2,5-dione-3,6-diyl and/or furo[3,2-b]furan-2,5-dione-3,6-diylrepeating units and their thioketone derivatives (the numbers in the first formula indicate the positions on the thienothiophene or furofuran core):

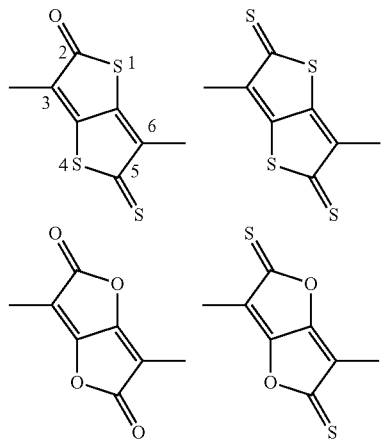

It was found that conjugated polymers based on these units show good processability and high solubility in organic solvents, and are thus especially suitable for large scale production using solution processing methods. At the same time, they show a low bandgap, high charge carrier mobility and high oxidative stability and are promising materials for organic electronic OE devices, especially for OPV devices.

Monomeric derivatives of thieno[3,2-b]thiophene-2,5-dione have been studied in redox systems (Guenther, Erhard; Huenig, Siegfried. *Chemische Berichte* 1992, 125, 1235-41), demonstrating the electron deficiency of such a core (i.e. electron accepting unit). Other monomeric derivatives of thieno[3,2-b]thiophene-2,5-dione have also been used as electrophotographic photoreceptors (Hayata, Hirofumi; Hirano, Akira; Hirose, Hisahiro. *Jpn. Kokai Tokkyo Koho* 1992, JP04338761 A 19921126.), demonstrating photosensitivity and charge transport properties. However, it has hitherto not been suggested to use such compounds as recurring units in semiconducting polymers, especially for use in OFET or OPV devices.

SUMMARY OF THE INVENTION

The invention relates to a conjugated polymer comprising one or more units of formula I

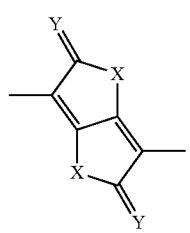

wherein X and Y are independently of each other S or O.

The unit of formula I preferably denotes thieno[3,2-b]thiophene-2,5-dione-3,6-diyl or furo[3,2-b]furan-2,5-dione-3,6-diyl, wherein the ketone functionality at the 2- and 5-positions can alternatively be a thioketone functionality, as represented by formulae Ia-Id:

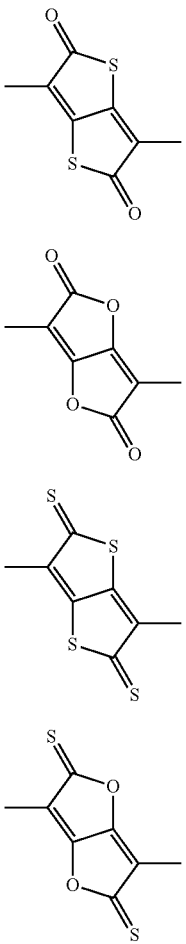

Especially preferred are units of formula Ia and Ib.

The invention further relates to a conjugated polymer comprising one or more repeating units, wherein said repeating units contain a unit of formula I and/or one or more groups selected from aryl and heteroaryl groups that are optionally substituted, and wherein at least one repeating unit in the polymer contains at least one unit of formula I.

The invention further relates to monomers containing a unit of formula I and further containing one or more reactive groups, which can be used for the preparation of conjugated polymers as described above and below.

The invention further relates to the use of units of formula I as electron acceptor units in semiconducting polymers.

The invention further relates to a semiconducting polymer comprising one or more units of formula I as electron acceptor units, and preferably further comprising one or more units having electron donor properties.

The invention further relates to the use of the polymers according to the present invention as electron acceptor component in semiconducting materials, formulations, blends, devices or components of devices.

The invention further relates to a semiconducting material, formulation, blend, device or component of a device comprising a polymer according to the present invention as electron acceptor component, and preferably further comprising one or more compounds or polymers having electron donor properties.

The invention further relates to a mixture or blend comprising one or more polymers according to the present invention and one or more additional compounds or polymers which are preferably selected from compounds and polymers having one or more of semiconducting, charge transport, hole or electron transport, hole or electron blocking, electrically conducting, photoconducting or light emitting properties.

The invention further relates to a formulation comprising one or more polymers, mixtures or blends according to the present invention and optionally one or more solvents, preferably selected from organic solvents.

The invention further relates to the use of polymers, mixtures, blends and formulations according to the present invention as charge transport, semiconducting, electrically conducting, photoconducting or light emitting material in optical, electrooptical, electronic, electroluminescent or photoluminescent components or devices.

The invention further relates to a charge transport, semiconducting, electrically conducting, photoconducting or light emitting material or component comprising one or more polymers, polymer blends of formulations according to the present invention.

The invention further relates to an optical, electrooptical or electronic component or device comprising one or more polymers, polymer blends, formulations, components or materials according to the present invention.

The optical, electrooptical, electronic electroluminescent and photoluminescent components or devices include, without limitation, organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

BRIEF DESCRIPTION OF THE DRAWINGS

FIG. 1 shows the current-voltage characteristic (A), linear mobility (B) and saturated mobility (C) for an OFET of Example 1.4.

DETAILED DESCRIPTION OF THE INVENTION

The monomers and polymers of the present invention are easy to synthesize and exhibit several advantageous properties, like a low bandgap, a high charge carrier mobility, a high solubility in organic solvents, a good processability for the device manufacture process, a high oxidative stability and a long lifetime in electronic devices.

In addition, they show the following advantageous properties:
i) The unit of formula I consists of two five-membered rings that are fused, and itself is contained within the backbone of the polymer. The pre-established quinoidal band structure of the units of formula I increases the quinoidal band structure of the resultant polymers, and therefore lowers the band gap of the resultant polymer, and thus results in improving the light harvesting ability of the material.

ii) Additional solubility can be introduced into the polymer by inclusion of co-units (like aryl or heteroaryl) containing solubilising groups.

iii) The units of formula I have planar structures that enable strong pi-pi stacking in the solid state leading to better improved charge transport properties in the form of higher charge carrier mobility.

iii) The addition of reactive functionality onto specific positions (3 and 6 positions) on the unit of formula I will enable the preparation of regioregular or random chemically polymerized homopolymers and copolymers. Such polymers can be obtained using Yamamoto, Suzuki or Stille coupling polymerization methods. By these preparative methods, the regioregular polymer will have higher structural order in the solid state compared to regioirregular materials synthesized using a non-selective polymerization method. This will lead to a polymer with higher charge carrier mobility for application in OFET and OPV devices.

iv) Additional fine-tuning of the electronic energies (HOMO/LUMO levels) by either careful selection of aryl or heteroaryl units (like $Ar^1$—$Ar^3$) on each side of the unit of formula I or co-polymerisation with appropriate co-monomer(s) should afford candidate materials for organic photovoltaic applications.

The synthesis of the unit of formula I, its functional derivatives, homopolymer, and co-polymers can be achieved based on methods that are known to the skilled person and described in the literature, as will be further illustrated herein.

Above and below, the term "polymer" generally means a molecule of high relative molecular mass, the structure of which essentially comprises the multiple repetition of units derived, actually or conceptually, from molecules of low relative molecular mass (PAC, 1996, 68, 2291). The term "oligomer" generally means a molecule of intermediate relative molecular mass, the structure of which essentially comprises a small plurality of units derived, actually or conceptually, from molecules of lower relative molecular mass (PAC, 1996, 68, 2291). In a preferred sense according to the present invention a polymer means a compound having >1, preferably ≥5 repeating units, and an oligomer means a compound with >1 and <10, preferably <5, repeating units.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (PAC, 1996, 68, 2291).

The term "leaving group" means an atom or group (charged or uncharged) that becomes detached from an atom in what is considered to be the residual or main part of the molecule taking part in a specified reaction (see also PAC, 1994, 66, 1134).

The term "conjugated" means a compound containing mainly C atoms with sp²-hybridisation (or optionally also sp-hybridisation), which may also be replaced by hetero atoms. In the simplest case this is for example a compound with alternating C—C single and double (or triple) bonds, but does also include compounds with units like 1,3-phenylene. "Mainly" means in this connection that a compound with naturally (spontaneously) occurring defects, which may lead to interruption of the conjugation, is still regarded as a conjugated compound.

Unless stated otherwise, the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, 1,2,4-trichlorobenzene is used as solvent. The degree of polymerization, also referred to as total number of repeating units, n, means the number average degree of polymerization given as $n=M_n/M_U$, wherein $M_n$ is the number average molecular weight and $M_U$ is the molecular weight of the single repeating unit, see J. M. G. Cowie, *Polymers: Chemistry & Physics of Modern Materials*, Blackie, Glasgow, 1991.

The term "carbyl group" as used above and below denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The term "hydrocarbyl group" denotes a carbyl group that does additionally contain one or more H atoms and optionally contains one or more hetero atoms like for example N, O, S, P, Si, Se, As, Te or Ge.

A carbyl or hydrocarbyl group comprising a chain of 3 or more C atoms may also be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1$-$C_{40}$ carbyl or hydrocarbyl group is acyclic, the group may be straight-chain or branched. The $C_1$-$C_{40}$ carbyl or hydrocarbyl group includes for example: a $C_1$-$C_{40}$ alkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_6$-$C_{12}$ aryl group, and a $C_4$-$C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

Aryl and heteroaryl preferably denote a mono-, bi- or tri-cyclic aromatic or heteroaromatic group with 4 to 30 ring C atoms that may also comprise condensed rings and is optionally substituted with one or more groups L, wherein L is selected from halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp, with R$^0$, R$^{00}$, P and Sp having the meanings given above and below.

Very preferred substituents L are selected from halogen, most preferably F, or alkyl, alkoxy, oxaalkyl, thioalkyl, fluoroalkyl and fluoroalkoxy with 1 to 12 C atoms or alkenyl, alkynyl with 2 to 12 C atoms.

Especially preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, pyridine, preferably 2- or 3-pyridine, pyrimidine, thiophene preferably 2-thiophene, selenophene, preferably 2-selenophene, thieno[3,2-b]thiophene, thiazole, thiadiazole, oxazole and oxadiazole, especially preferably thiophene-2-yl, 5-substituted thiophene-2-yl or pyridine-3-yl, all of which can be unsubstituted, mono- or polysubstituted with L as defined above.

An alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

An alkenyl group, wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably straight-chain perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

The above-mentioned alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-meth-oxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In another preferred embodiment of the present invention, $R^1$ is selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

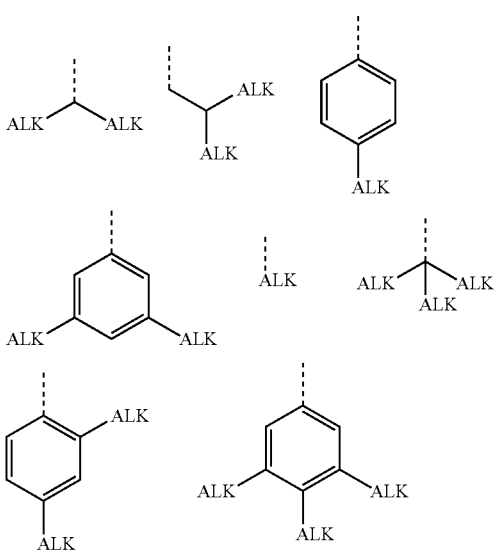

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

—CY$^1$=CY$^2$— is preferably —CH=CH—, —CF=CF— or —CH=C(CN)—.

Halogen is F, Cl, Br or I, preferably F, Cl or Br.

—CO—, —C(=O)— and —C(O)— denote a carbonyl group, i.e.

The polymers may also be substituted with a polymerisable or crosslinkable reactive group, which is optionally protected during the process of forming the polymer. Particular preferred polymers of this type are those of formula I wherein R$^1$ denotes P-Sp. These polymers are particularly useful as semiconductors or charge transport materials, as they can be crosslinked via the groups P, for example by polymerisation in situ, during or after processing the polymer into a thin film for a semiconductor component, to yield crosslinked polymer films with high charge carrier mobility and high thermal, mechanical and chemical stability.

Preferably the polymerisable or crosslinkable group P is selected from $CH_2$=CW$^1$—C(O)—O—, $CH_2$=CW$^1$—C(O)—,

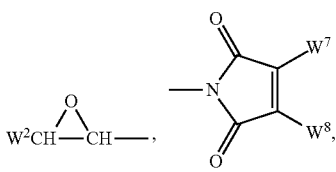

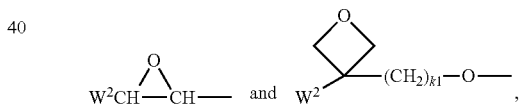

$CH_2$=CW$^2$—(O)$_{k1}$—, CW$^1$=CH—C(O)—(O)$_{k3}$—, CW$^1$=CH—C(O)—NH—, $CH_2$=CW$^1$—C(O)—NH—, $CH_3$—CH=CH—O—, ($CH_2$=CH)$_2$CH—OC(O)—, ($CH_2$=CH—$CH_2$)$_2$CH—O—C(O)—, ($CH_2$=CH)$_2$CH—O—, ($CH_2$=CH—$CH_2$)$_2$N—, ($CH_2$=CH—$CH_2$)$_2$N—C(O)—, HO—CW$^2$W$^3$—, HS—CW$^2$W$^3$—, HW$^2$N—, HO—CW$^2$W$^3$—NH—, $CH_2$=CH—(C(O)—O)$_{k1}$-Phe-(O)$_{k2}$—, $CH_2$=CH—(C(O))$_{k1}$-Phe-(O)$_{k2}$—, Phe-CH=CH—, HOOC—, OCN—, and W$^4$W$^5$W$^6$Si—, with W$^1$ being H, F, Cl, CN, CF$_3$, phenyl or alkyl with 1 to 5 C-atoms, in particular H, C$_1$ or CH$_3$, W$^2$ and W$^3$ being independently of each other H or alkyl with 1 to 5 C-atoms, in particular H, methyl, ethyl or n-propyl, W$^4$, W$^5$ and W$^6$ being independently of each other Cl, oxaalkyl or oxacarbonylalkyl with 1 to 5 C-atoms, W$^7$ and W$^8$ being independently of each other H, Cl or alkyl with 1 to 5 C-atoms, Phe being 1,4-phenylene that is optionally substituted by one or more groups L as defined above, k$_1$, k$_2$ and k$_3$ being independently of each other 0 or 1, k$_3$ preferably being 1, and k$_4$ being an integer from 1 to 10.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are $CH_2$=CH—C(O)—O—, $CH_2$=C(CH$_3$)—C(O)—O—, $CH_2$=CF—C(O)—O—, $CH_2$=CH—O—, ($CH_2$=CH)$_2$CH—O—C(O)—, ($CH_2$=CH)$_2$CH—O—, or protected derivatives thereof. Further preferred groups P are selected from the group consisting of vinyloxy, acrylate, methacrylate, fluoroacrylate, chloroacrylate, oxetan and epoxy groups, very preferably from an acrylate or methacrylate group.

Polymerisation of group P can be carried out according to methods that are known to the ordinary expert and described in the literature, for example in D. J. Broer; G. Challa; G. N. Mol, *Macromol. Chem.*, 1991, 192, 59.

The term "spacer group" is known in prior art and suitable spacer groups Sp are known to the ordinary expert (see e.g. Pure Appl. Chem. 73(5), 888 (2001). The spacer group Sp is preferably of formula Sp'-X', such that P-Sp- is P-Sp'-X'—, wherein Sp' is alkylene with up to 30 C atoms which is unsubstituted or mono- or polysubstituted by F, Cl, Br, I or CN, it being also possible for one or more non-adjacent $CH_2$ groups to be replaced, in each case independently from one another, by —O—, —S—, —NH—, —NR$^0$—, —SiR$^0$R$^{00}$—, —C(O)—, —C(O)O—, —OC(O)—, —OC(O)—O—, —S—C(O)—, —C(O)—S—, —CH=CH— or —C≡C— in such a manner that O and/or S atoms are not linked directly to one another, X' is —O—, —S—, —C(O)—, —C(O)O—, —OC(O)—, —O—C(O)O—, —C(O)—NR⁰—, —NR⁰—C(O)—, —NR⁰—C(O)—NR⁰⁰—, —OCH₂—, —CH₂O—, —SCH₂—, —CH₂S—, —CF₂O—, —OCF₂—, —CF₂S—, —SCF₂—, —CF₂CH₂—, —CH₂CF₂—, —CF₂CF₂—, —CH=N—, —N=CH—, —N=N—, —CH=CR⁰—, —CY¹=CY²—, —C≡C—, —CH=CH—C(O)O—, —OC(O)—CH=CH— or a single bond, R⁰ and R⁰⁰ are independently of each other H or alkyl with 1 to 12 C-atoms, and Y¹ and Y² are independently of each other H, F, Cl or CN.

X' is preferably —O—, —S—, —OCH₂—, —CH₂O—, —SCH₂—, —CH₂S—, —CF₂O—, —OCF₂—, —CF₂S—, —SCF₂—, —CH₂CH₂—, —CF₂CH₂—, —CH₂CF₂—, —CF₂CF₂—, —CH=N—, —N=CH—, —N=N—, —CH=CR⁰—, —CY¹=CY²—, —C≡C— or a single bond, in particular —O—, —S—, —C≡C—, —CY¹=CY²— or a single bond. In another preferred embodiment X' is a group that is able to form a conjugated system, such as —C≡C— or —CY¹=CY²—, or a single bond.

Typical groups Sp' are, for example, —(CH₂)ₚ—, —(CH₂CH₂O)_q—CH₂CH₂—, —CH₂CH₂—S—CH₂CH₂— or —CH₂CH₂—NH—CH₂CH₂— or —(SiR⁰R⁰⁰—O)ₚ—, with p being an integer from 2 to 12, q being an integer from 1 to 3 and R⁰ and R⁰⁰ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Preferably R¹ is are selected from straight-chain, branched or cyclic alkyl with 1 to 35 C atoms, in which one or more non-adjacent C atoms are optionally replaced by —O—, —S—, —C(O)—, —C(O)—O—, —O—C(O)—, —O—C(O)—O—, —CR⁰=CR⁰⁰— or —C≡C— and in which one or more H atoms are optionally replaced by F, Cl, Br, I or CN, or denote aryl, heteroaryl, aryloxy, heteroaryloxy, arylcarbonyl, heteroarylcarbonyl, arylcarbonyloxy, heteroarylcarbonyloxy, aryloxycarbonyl or heteroaryloxycarbonyl having 4 to 30 ring atoms that is unsubstituted or substituted by one or more non-aromatic groups L as defined above.

Preferred polymers according to the present invention contain one or more repeating units of formula I1:

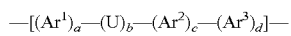    I1 wherein

U is a unit of formula I, preferably selected of formulae Ia-Id,

Ar¹, Ar², Ar³ are, on each occurrence identically or differently, and independently of each other, aryl or heteroaryl, preferably having 5 to 30 ring atoms, which is optionally substituted, preferably by one or more groups R¹, R¹ is on each occurrence identically or differently F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms, or P-Sp-, R⁰ and R⁰⁰ are independently of each other H or optionally substituted C₁₋₄₀ carbyl or hydrocarbyl, P is a polymerisable or crosslinkable group, Sp is a spacer group or a single bond, X⁰ is halogen, preferably F, Cl or Br, a, b, c and d are on each occurrence identically or differently 0, 1 or 2, wherein in at least one repeating unit b is 1.

Further preferred polymers according to the present invention contain, further to the units of formula I or I1, one or more additional repeating units selected from monocyclic or polycyclic aryl or heteroaryl groups that are optionally substituted.

These additional repeating units are preferably selected of formula II

    II wherein Ar¹, Ar², Ar³, a, b, c and d are as defined in formula I1, and M is an aryl or heteroaryl group having 5 to 30 ring atoms, which is optionally substituted by one or more groups R¹ as defined above and below, and is preferably selected from aryl or heteroaryl groups having electron acceptor properties.

The conjugated polymers according to the present invention are preferably selected of formula III:

    III wherein

A is a unit of formula I or I1 or its preferred subformulae,

B is a unit comprising one or more aryl or heteroaryl groups that are optionally substituted, preferably selected of formula II, x is >0 and ≤1, Y is ≥0 and <1, x+y is 1, and n is an integer >1.

Preferred polymers of formula III are selected of formula IIIa

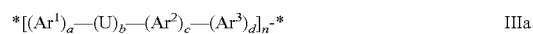    IIIa wherein U, Ar¹, Ar², Ar³, a, b, c and d are as defined in formula II and n is as defined in formula III, and wherein the individual repeating units [(Ar¹)_a—(U)_b-(Ar²)_c—(Ar³)_d] in the polymer can be identical or different from one another.

Further preferred polymers of formula III are selected of formula IIIb

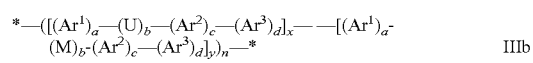    IIIb wherein U, Ar¹, Ar², Ar³, a, b, c and d are as defined in formula II, M is as defined in formula II, and x, y and n are as defined in formula III.

Preferred polymers of formula III are selected of formula IV

    IV wherein A, B, x, y and n are as defined in formula III, and R² and R³ have independently of each other one of the meanings of R¹, preferably F, Br or Cl, or denote H, —CH₂Cl, —CHO, —CH=CH₂, —SiR'R''R''', —SnR'R''R''', —BR'R'', —B(OR')(OR''), —B(OH)₂, or P-Sp, wherein P and Sp are as defined above, and R', R'' and R''' have independently of each other one of the meanings of R⁰ defined above, and two of R', R'' and R''' may also form a ring together with the hetero atom to which they are attached.

Preferred polymers of formula IV are selected of formula IVa and IVb

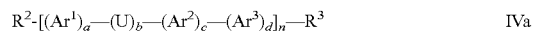    IVa

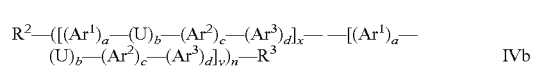    IVb wherein U, Ar$^1$, Ar$^2$, Ar$^3$, a, b, c and d are as defined in formula II, M is as defined in formula II, x, y and n are as defined in formula III, and R$^2$ and R$^3$ are as defined in formula IV.

In the polymers according to the present invention, the total number of repeating units n is preferably from 2 to 10,000. The total number of repeating units n is preferably ≥5, very preferably ≥10, most preferably ≥50, and preferably ≤500, very preferably ≤1,000, most preferably ≤2,000, including any combination of the aforementioned lower and upper limits of n.

The polymers of the present invention include homopolymers and copolymers, like statistical or random copolymers, alternating copolymers and block copolymers, as well as combinations thereof.

In the polymers represented by formula III or IV or their subformulae, x denotes the mole fraction of units A, y denotes the mole fraction of units B, and n denotes the degree of polymerisation or total number of units A and B. These formulae includes block copolymers, random or statistical copolymers and alternating copolymers of A and B, as well as homopolymers of A for the case when x is >0 and y is 0.

Thus, in the polymers of the present invention the individual repeating units can be selected independently of each other, so that a polymer may comprise identical and/or different repeating units. The polymers thus include homopolymers and copolymers like for example statistically or random copolymers, for example with a monomer sequence such as —Ar$^1$—U—U—Ar$^2$—U—Ar$^3$—Ar$^1$—Ar$^2$—Ar$^3$-M-, random or alternating copolymers of units (Ar$^1$—U—Ar$^2$—Ar$^3$) and units (Ar$^1$-M-Ar$^2$—Ar$^3$), alternating copolymers, for example with a sequence such as —Ar$^1$—U—Ar$^1$—U—Ar$^1$—U—, —Ar$^1$—U—Ar$^2$—Ar$^1$—U—Ar$^2$— or —Ar$^1$—U—Ar$^2$—Ar$^3$—Ar$^1$—U—Ar$^2$—Ar$^3$, which can also be regarded as homopolymers of the repeating units (Ar$^1$—U), (Ar$^1$—U—Ar$^2$) and (Ar$^1$—U—Ar$^2$—Ar$^3$), respectively, or with a sequence such as —(Ar$^1$—U—Ar$^2$)—(Ar$^1$—U)—(Ar$^1$—U—Ar$^2$)—(Ar$^1$—U)—, and block copolymers, for example with a sequence such as —Ar$^1$—Ar$^1$—U—U—U—U—Ar$^2$—Ar$^2$—Ar$^2$—Ar$^3$—Ar$^3$—Ar$^3$—Ar$^3$ (if Ar$^1$, U, Ar$^2$ and Ar$^3$ are regarded as the repeating units) or with a sequence such as —(Ar$^1$—U)—(Ar$^1$—U)—(Ar$^1$—U)—(Ar$^1$—U—Ar$^2$)—(Ar$^1$—U—Ar$^2$)—(Ar$^1$—U—Ar$^2$) (if e.g. (Ar$^1$—U) and (Ar$^1$—U—Ar$^2$) are regarded as the repeating units), wherein the groups Ar$^1$, U, Ar$^2$ and Ar$^3$ together form a conjugated system, and wherein in addition groups occurring more than once (for example each group Ar$^1$ in the sequence —Ar$^1$—Ar$^1$—Ar$^1$—) can be identical or different from one another.

Especially preferred are polymers of the formula (Ar$^1$—U)$_n$, (Ar$^1$—U—Ar$^2$)$_n$, (Ar$^1$—U—Ar$^3$)$_n$, (Ar$^1$—U—Ar$^2$—Ar$^3$)$_n$ consisting of identical repeating units.

Further preferred are copolymers of the following formulae

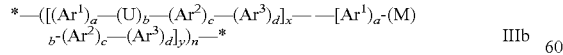

IIIb

IIIc

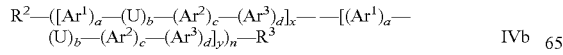

IVb

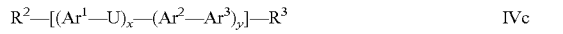

IVc wherein U, Ar$^1$, Ar$^2$, Ar$^3$, a, b, c and d are as defined in formula II, M is as defined in formula II, and x, y and n are as defined in formula III, wherein these polymers can be alternating or random copolymers.

Another aspect of the invention relates to monomers of formula V

V wherein U, Ar$^1$, Ar$^2$, R$^2$ and R$^3$ have the meanings of formula II and IV, or one of the preferred meanings as described above and below.

Especially preferred are monomers of formula V wherein R$^2$ and R$^3$ are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH and —Sn(Z$^4$)$_3$, wherein Z$^{1-4}$ are selected from the group consisting of alkyl and aryl, each being optionally substituted, and two groups Z$^2$ may also form a cyclic group.

Preferably the repeating units, monomers and polymers of formulae I, I1, II, II, IV, V and their subformulae are selected from the following list of preferred embodiments:

y is ≥0 and ≤1,
b=d=1 and a=c=0, preferably in all repeating units,
a=b=c=d=1, preferably in all repeating units,
a=b=d=1 and c=0, preferably in all repeating units,
a=b=c=1 and d=0, preferably in all repeating units,
a=c=2, b=1 and d=0, preferably in all repeating units,
a=c=2 and b=d=1, preferably in all repeating units, Ar$^1$ and Ar$^2$ are selected from the group consisting of thiophene-2,5-diyl, thiazole-2,5-diyl, selenophene-2,5-diyl, furan-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, or selenopheno[2,3-b]thiophene-2,5-diyl, 2,2'-bithiophene-5,5'-diyl all of which are unsubstituted, or mono- or polysubstituted, preferably with R$^1$ as defined above and below, Ar$^3$ is selected from the group consisting of 1,4-phenylene, 2,3-dicyano-1,4-phenylene, 2,5-dicyano, 2,3-difluoro-1,4-phenylene, 2,5-difluoro-1,4-phenylene, 2,3,5,6-tetrafluoro, 3,4-difluorothiophene-2,5-diyl, pyridine-2,5-diyl, pyrimidine-2,5-diyl, naphthalene-2,6-diyl, thiophene-2,5-diyl, furan-2,5-diyl, selenophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, benzo[1,2-b:4,5-b']dithiophene-2,6-diyl, benzo[2,1-b;3,4-b']dithiophene-2,7-diyl, 2,2-dithiophene, 2,2-diselenophene, dithieno[3,2-b:2',3'-d]silole-5,5-diyl, dithieno[3,2-b;2',3'-d]pyrrole-5,5-diyl, 4H-cyclopenta[2,1-b:3,4-b']dithiophene-2,6-diyl, carbazole-2,7-diyl, fluorene-2,7-diyl, indaceno[1,2-b:5,6-b']dithiophene-2,7-diyl, benzo[1'',2'':4,5;4'',5'':4',5]bis(silolo[3,2-b:3',2'-b]thiophene)-2,7-diyl, phenanthro[1,10,9,8-c,d,e,f,g]carbazole-2,7-diyl, dihydrobenzo[def]carbazole-2,7-diyl, benzo[2,1,3]thiadiazole-4,7-diyl, benzo[2,1,3]selenadiazole-4,7-diyl, benzo[2,1,3]oxadiazole-4,7-diyl, 2H-benzotriazole-4,7-diyl, quinoxaline-5,8-diyl, thieno[3,4-b]pyrazine-2,5-diyl, thieno[3,4-b]thiophene-4,6-diyl, thieno[3,4-b]thiophene-6,4-diyl, thieno[2,1,3]thiadiazole-2,5-diyl, pyrrolo[3,4-c]pyrrole-1,4-dione-3,6-diyl, or [1,3]thiazolo[5,4-d][1,3]thiazole-2,5-diyl, thieno[3,4-c]pyrrole-4,6-dione-1,3- diyl, 4-oxa-1,8-dithia-as-indacene-2,7-diyl, benzo[c]chromene-3,8-diyl, all of which are unsubstituted, or mono- or polysubstituted, preferably with $R^1$ as defined above and below, M is selected from the group consisting of 1,4-phenylene, 2,3-dicyano-1,4-phenylene, 2,5-dicyano, 2,3-difluoro-1,4-phenylene, 2,5-difluoro-1,4-phenylene, 2,3,5,6-tetrafluoro, 3,4-difluorothiophene-2,5-diyl, pyridine-2,5-diyl, pyrimidine-2,5-diyl, naphthalene-2,6-diyl, thiophene-2,5-diyl, furan-2,5-diyl, selenophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, benzo[1,2-b:4,5-b']dithiophene-2,6-diyl, benzo[2,1-b;3,4-b']dithiophene-2,7-diyl, 2,2-dithiophene, 2,2-diselenophene, dithieno[3,2-b:2',3'-d]silole-5,5-diyl, dithieno[3,2-b;2',3'-d]pyrrole-5,5-diyl, 4H-cyclopenta[2,1-b:3,4-b']dithiophene-2,6-diyl, carbazole-2,7-diyl, fluorene-2,7-diyl, indaceno[1,2-b:5,6-b']dithiophene-2,7-diyl, benzo[1",2":4,5;4",5":4',5]bis(silolo[3,2-b:3',2'-b]thiophene)-2,7-diyl, phenanthro[1,10,9,8-c,d,e,f,g]carbazole-2,7-diyl, dihydrobenzo[def]carbazole-2,7-diyl, benzo[2,1,3]thiadiazole-4,7-diyl, benzo[2,1,3]selenadiazole-4,7-diyl, benzo[2,1,3]oxadiazole-4,7-diyl, 2H-benzotriazole-4,7-diyl, quinoxaline-5,8-diyl, thieno[3,4-b]pyrazine-2,5-diyl, thieno[3,4-b]thiophene-4,6-diyl, thieno[3,4-b]thiophene-6,4-diyl, thieno[2,1,3]thiadiazole-2,5-diyl, pyrrolo[3,4-c]pyrrole-1,4-dione-3,6-diyl, or [1,3]thiazolo[5,4-d][1,3]thiazole-2,5-diyl, thieno[3,4-c]pyrrole-4,6-dione-1,3-diyl, 4-oxa-1,8-dithia-as-indacene-2,7-diyl, benzo[c]chromene-3,8-diyl, all of which are unsubstituted, or mono- or polysubstituted, preferably with $R^1$ as defined above and below, n is at least 5, preferably at least 10, very preferably at least 50, and up to 2,000, preferably up to 500.

$M_w$ is at least 5,000, preferably at least 8,000, very preferably at least 10,000, and preferably up to 300,000, very preferably up to 100,000, $R^1$ is selected from the group consisting of primary alkyl or alkoxy with 1 to 30 C atoms, secondary alkyl or alkoxy with 3 to 30 C atoms, and tertiary alkyl or alkoxy with 4 to 30 C atoms, wherein in all these groups one or more H atoms are optionally replaced by F, $R^1$ is selected from the group consisting of aryl, heteroaryl, aryloxy, heteroaryloxy, each of which is optionally alkylated or alkoxylated and has 4 to 30 ring atoms, $R^1$ is F, Cl, Br, I, CN, $R^4$, —C(O)—$R^4$, —C(O)—O—$R^4$, or —O—C(O)—$R^4$, wherein $R^4$ is straight-chain, branched or cyclic alkyl with 1 to 30 C atoms, in which one or more non-adjacent C atoms are optionally replaced by —O—, —S—, —C(O)—, —C(O)—O—, —O—C(O)—, —O—C(O)—O—, —CR$^0$=CR$^{00}$— or —C≡C— and in which one or more H atoms are optionally replaced by F, Cl, Br, I or CN, or $R^1$ is aryl, aryloxy, heteroaryl or heteroaryloxy having 4 to 30 ring atoms which is unsubstituted or which is substituted by one or more halogen atoms or by one or more groups $R^4$, —C(O)—$R^4$, —C(O)—O—$R^4$, or —O—C(O)—$R^4$ as defined above, $R^4$ is primary alkyl with 1 to 30 C atoms, very preferably with 1 to 15 C atoms, secondary alkyl with 3 to 30 C atoms, or tertiary alkyl with 4 to 30 C atoms, wherein in all these groups one or more H atoms are optionally replaced by F, $R^0$ and $R^{00}$ are selected from H or $C_1$-$C_{10}$-alkyl, $R^2$ and $R^3$ are selected from H, halogen, —CH$_2$Cl, —CHO, —CH=CH$_2$—SiR'R"R'", —SnR'R"R'", —BR'R", —B(OR')(OR"), —B(OH)$_2$, P-Sp, $C_1$-$C_{20}$-alkyl, $C_1$-$C_{20}$-alkoxy, $C_2$-$C_{20}$-alkenyl, $C_1$-$C_{20}$-fluoroalkyl and optionally substituted aryl or heteroaryl, $R^2$ and $R^3$ are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^4$)$_2$, —C≡CH and —Sn(Z$^4$)$_3$, wherein $Z^{1-4}$ are selected from the group consisting of alkyl and aryl, each being optionally substituted, and two groups $Z^2$ may also form a cyclic group, very preferably from Br.

Preferred polymers of formula III are selected from the group consisting of the following formulae:

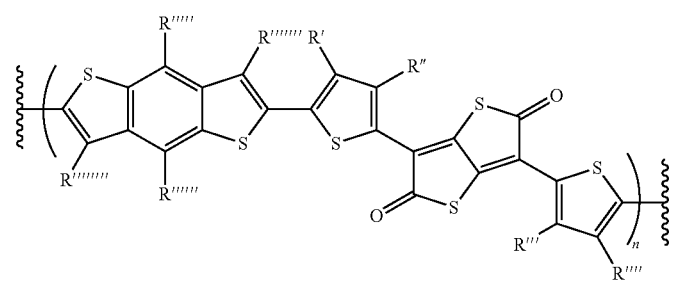

III1

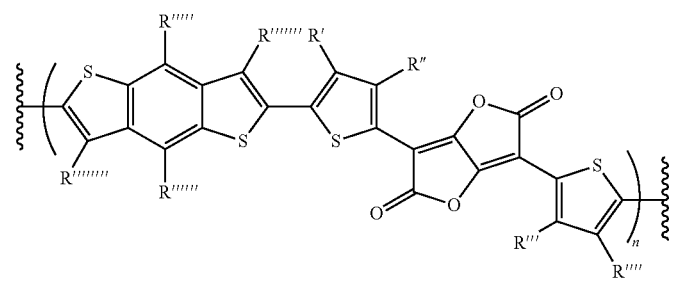

III2

-continued
III3
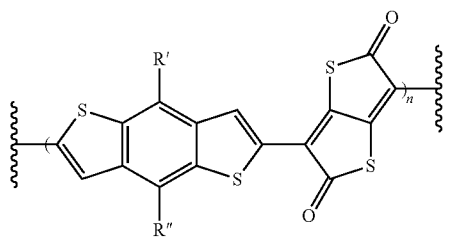
III4
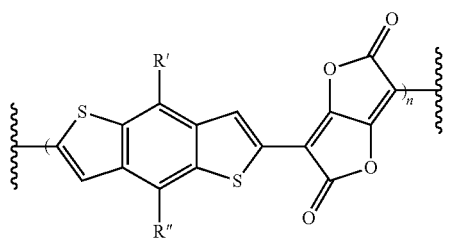
III5
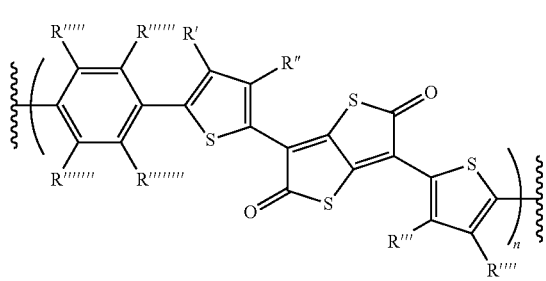
III6
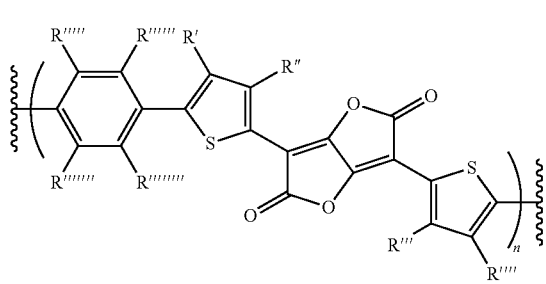
III7
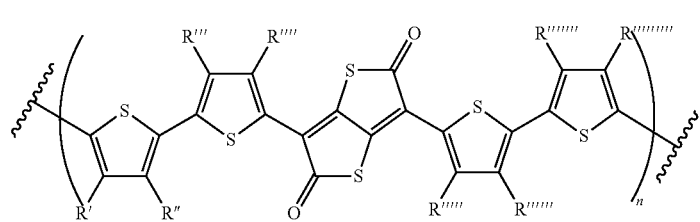
III8
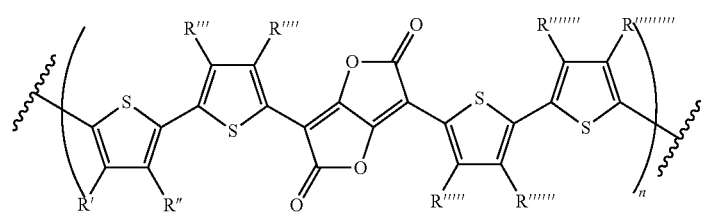

-continued
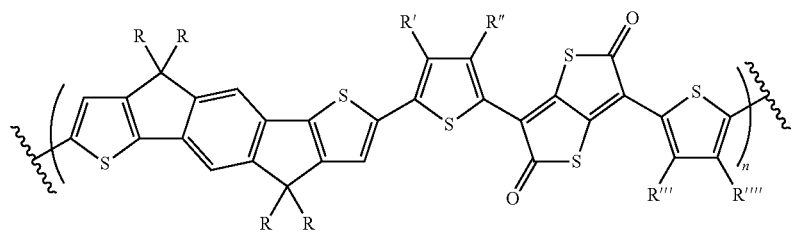
III9
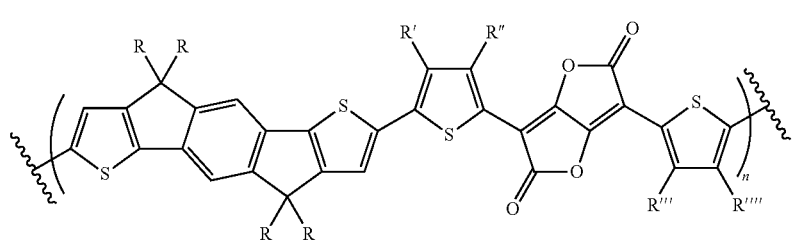
III10
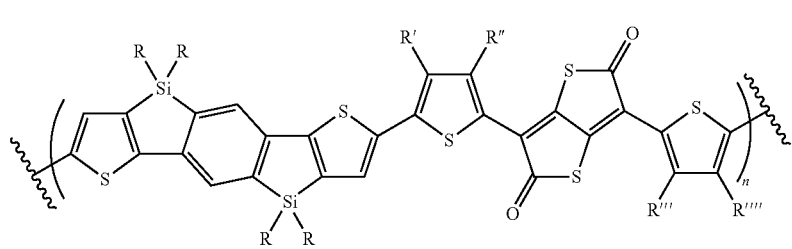
III11
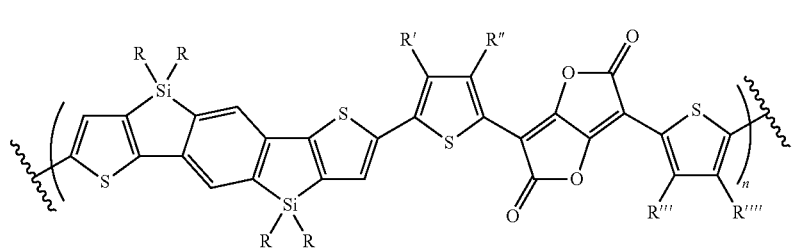
III12
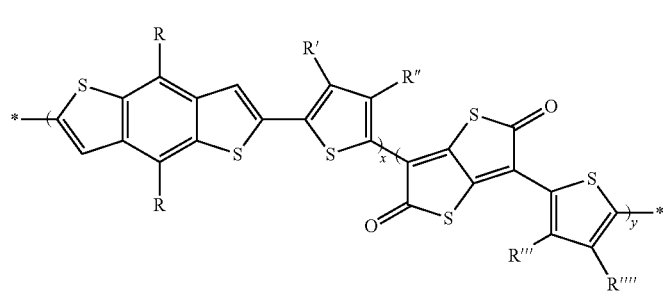
III13
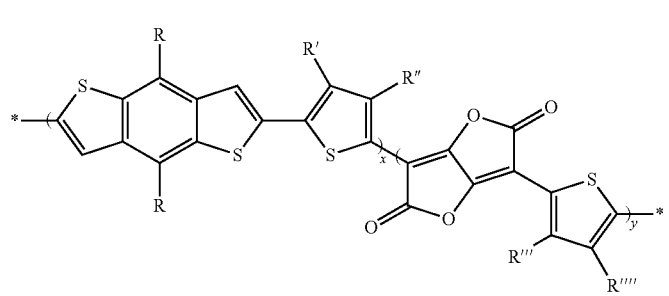
III14

-continued
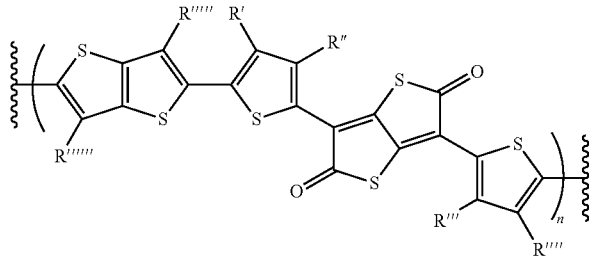
III15
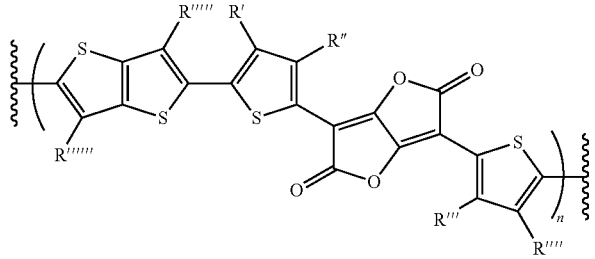
III16
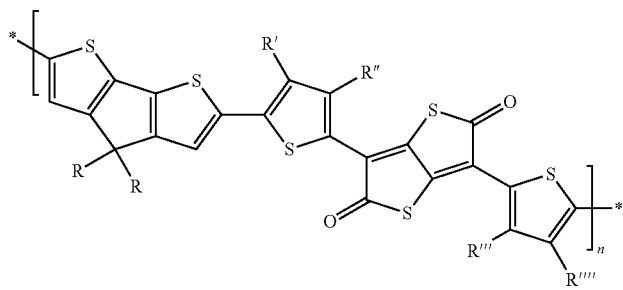
III17
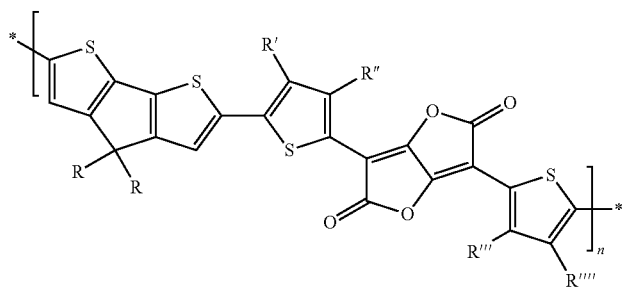
III18
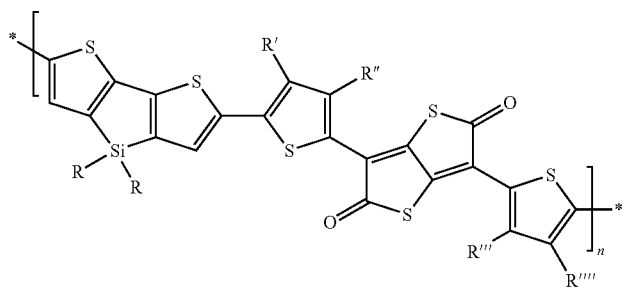
III19

III20
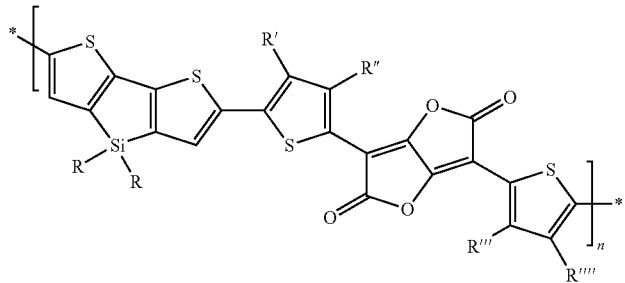
III21
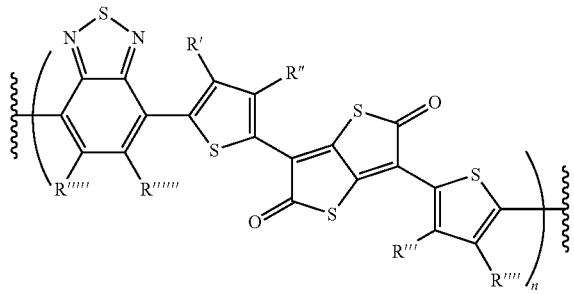
III22
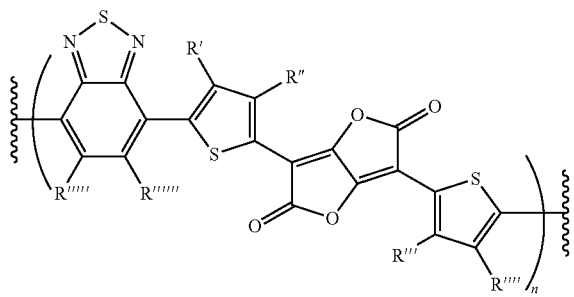
III23
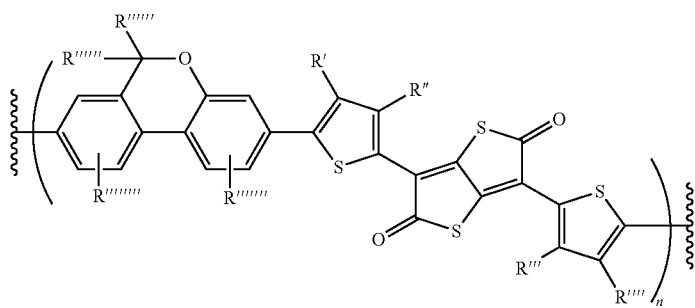
III24
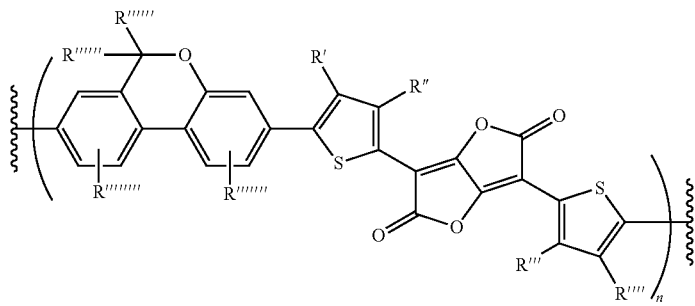

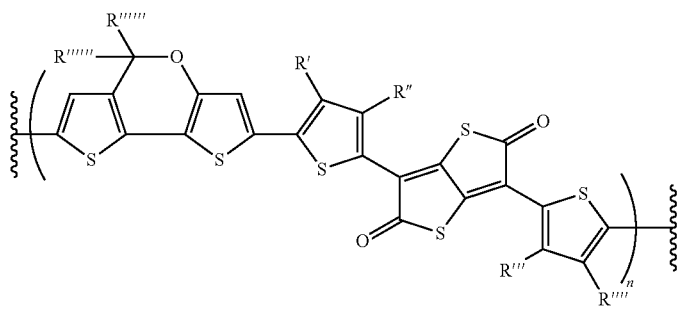

III25

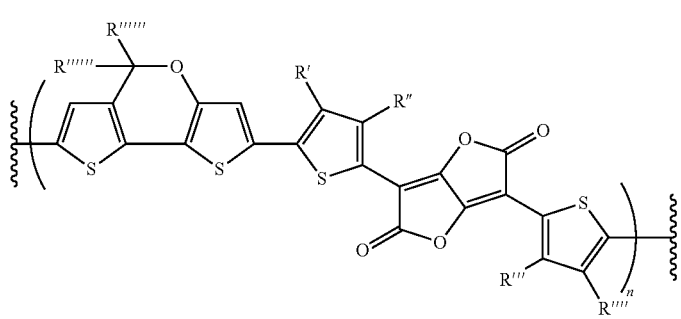

III26 wherein n, x and y have one of the meanings given in formula III or one of the preferred meanings given above and below, and R, R', R", R''', R'''', R''''', R'''''', R''''''' and R'''''''', on each occurrence identically or differently, and independently of one another, denote H or have one of the meanings of $R^1$ given in formula II or one of the preferred meanings of $R^1$ given above and below.

In formulae III1-III26 R, R', R", R''', R'''', R''''', R'''''', R''''''' and R'''''''', when being different from H, are preferably selected from the group consisting of primary alkyl or alkoxy with 1 to 30 C atoms, secondary alkyl or alkoxy with 3 to 30 C atoms, and tertiary alkyl or alkoxy with 4 to 30 C atoms, wherein in all these groups one or more H atoms are optionally replaced by F.

Further Preferred polymers of formula III are selected of the formula $$R^2\text{-chain-}R^3$$

wherein "chain" is a polymer chain selected from above formulae III1-III26, and $R^2$ and $R^3$ have one of the meanings given in formula IV or one of the preferred meanings given above and below.

The polymers of the present invention can be synthesized according to or in analogy to methods that are known to the skilled person and are described in the literature. Other methods of preparation can be taken from the examples. For example, they can be suitably prepared by aryl-aryl coupling reactions, such as Yamamoto coupling, Suzuki coupling, Stille coupling, Sonogashira coupling, Heck coupling or Buchwald coupling. Suzuki coupling, Stille coupling and Yamamoto coupling are especially preferred.

The monomers which are polymerised to form the repeat units of the polymers can be prepared according to methods which are known to the person skilled in the art.

Preferably the polymers are prepared from monomers of formula Ia or its preferred embodiments as described above and below.

Another aspect of the invention is a process for preparing a polymer by coupling one or more identical or different monomeric units of formula I or monomers of formula Ia with each other and/or with one or more comonomers in a polymerisation reaction, preferably in an aryl-aryl coupling reaction.

Suitable and preferred comonomers are those of the formula $$R^2\text{—}Ar^3\text{—}R^3$$

wherein $R^2$ and $R^3$ have one of the meanings of formula IV or one of the preferred meanings given above and below, and $Ar^3$ has one of the meanings of formula II or one of the preferred meanings given above and below.

Preferred methods for polymerisation are those leading to C—C-coupling or C—N-coupling, like Suzuki polymerisation, as described for example in WO 00/53656, Yamamoto polymerisation, as described in for example in T. Yamamoto et al., Progress in Polymer Science 1993, 17, 1153-1205 or in WO 2004/022626 A1, and Stille coupling. For example, when synthesizing a linear polymer by Yamamoto polymerisation, monomers as described above having two reactive halide groups $R^2$ and $R^3$ is preferably used. When synthesizing a linear polymer by Suzuki polymerisation, preferably a monomer as described above is used wherein at least one reactive group $R^2$ or $R^3$ is a boronic acid or boronic acid derivative group.

Suzuki polymerisation may be used to prepare homopolymers as well as statistical, alternating and block random copolymers. Statistical or block copolymers can be prepared for example from the above monomers of formula V wherein one of the reactive groups $R^2$ and $R^3$ is halogen and the other reactive group is a boronic acid or boronic acid derivative group. The synthesis of statistical, alternating and block copolymers is described in detail for example in WO 03/048225 A2 or WO 2005/014688 A2.

Suzuki polymerisation employs a Pd(0) complex or a Pd(II) salt. Preferred Pd(0) complexes are those bearing at least one phosphine ligand such as Pd(Ph₃P)₄. Another preferred phosphine ligand is tris(ortho-tolyl)phosphine, i.e. Pd(o-Tol)₄. Preferred Pd(II) salts include palladium acetate, i.e. Pd(OAc)₂. Suzuki polymerisation is performed in the presence of a base, for example sodium carbonate, potassium phosphate or an organic base such as tetraethylammonium carbonate. Yamamoto polymerisation employs a Ni(0) complex, for example bis(1,5-cyclooctadienyl)nickel(0).

As alternatives to halogens as described above, leaving groups of formula —O—SO₂Z¹ can be used wherein Z¹ is as described above. Particular examples of such leaving groups are tosylate, mesylate and triflate.

Especially suitable and preferred synthesis methods of the repeating units, monomers, and polymers of formula I, I1, II, III, IV and V are illustrated in the synthesis schemes shown hereinafter, wherein Ar¹, Ar² and Ar³ are as defined in formula II.

The preparation of the 3,6-dibromo-thieno[3,2-b]thiophene-2,5-dione and 3,6-diiodo-thieno[3,2-b]thiophene-2,5-dione has been described in Guenther, Erhard; Huenig, Siegfried. *Chemische Berichte* 1992, 125, 1235-41. The preparation of 3,6-dibromo-furo[3,2-b]furan-2,5-dione has been described in Stachel, Hans-Dietrich; Jungkenn, Michael; Koser-Gnoss, Christiane; Poschenrieder, Hermann; Redlin, Jutta. *Liebigs Annalen der Chemie* 1994, 961-4. Alternatively, the generic preparation of symmetric and asymmetric of 3,6-diaryl-furo[3,2-b]furan-2,5-dione core has been described, for example, in U.S. Pat. No. 3,780,064.

A synthesis scheme for further functionalisation of thieno[3,2-b]thiophene-2,5-dione core is shown in Scheme 1 and 2, wherein X is halogen, like for example iodine or bromine or X is a sulfonate, like for example trifate or nonaflate. The corresponding furo[3,2-b]furan-2,5-dione core can be functionalised in analogy thereto.

Scheme 1

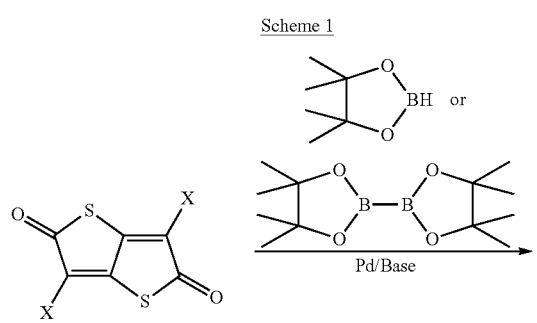

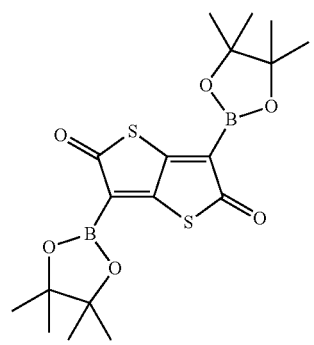

Scheme 2

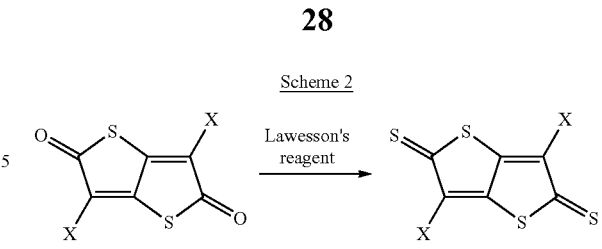

Synthesis schemes for the co-polymerisation of thieno[3,2-b]thiophene-2,5-dione are shown in Scheme 3 and 4. The corresponding copolymers of furo[3,2-b]furan-2,5-dione can be prepared in analogy thereto.

Scheme 3

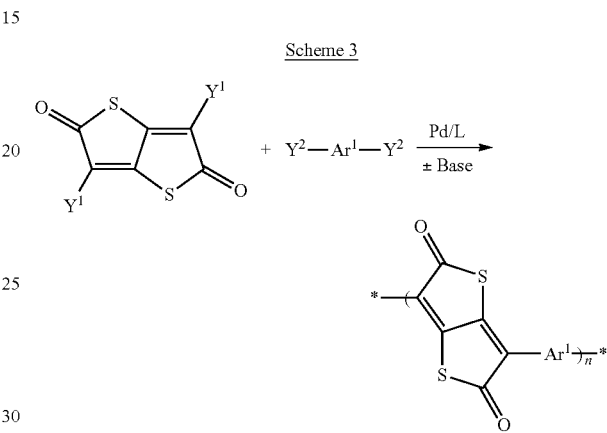

Y1 = Br/I; Y2 = B(OR)₂
Y1 = Br/I; Y2 = SnR₃
Y1 = B(OR)₂; Y2 = Br/I

Scheme 4

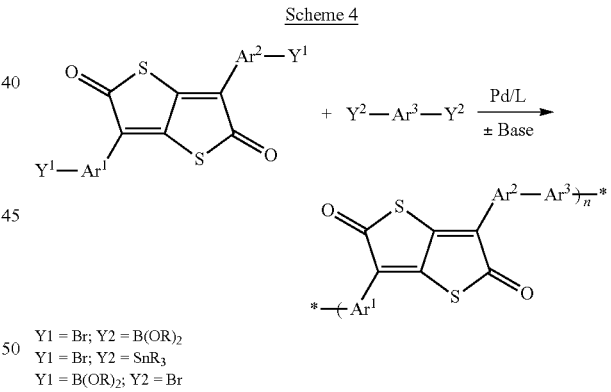

Y1 = Br; Y2 = B(OR)₂
Y1 = Br; Y2 = SnR₃
Y1 = B(OR)₂; Y2 = Br

The novel methods of preparing monomers and polymers as described above and below are another aspect of the invention.

The polymers according to the present invention can also be used in mixtures or polymer blends, for example together with monomeric compounds or together with other polymers having charge-transport, semiconducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising one or more polymers, mixtures or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxybenzene, 1-methylnaphthalene, N-methylpyrrolidinone, 3-fluorobenzotrifluoride, benzotrifluoride, benzotrifluoride, diosane, trifluoromethoxybenzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents with high boiling temperatures and solvent mixtures are preferred. For spin coating alkylated benzenes like xylene and toluene are preferred.

Examples of especially preferred solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and/or mixtures thereof.

The concentration of the polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 38, No 496, 296 (1966)". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, letter-press printing, screen printing, doctor blade coating, roller printing, reverse-roller printing, offset lithography printing, flexographic printing, web printing, spray coating, brush coating or pad printing. Ink-jet printing is particularly preferred as it allows high resolution layers and devices to be prepared.

Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents methoned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the polymer, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymers or formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The polymers according to the present invention are useful as charge transport, semiconducting, electrically conducting, photoconducting or light mitting materials in optical, electrooptical, electronic, electroluminescent or photoluminescent components or devices. In these devices, the polymers of the present invention are typically applied as thin layers or films.

Thus, the present invention also provides the use of the semiconducting polymer, polymer blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a polymer, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a polymer, polymer blend, formulation or organic semiconducting layer according to the present invention. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs and OPV devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV devices the polymer according to the present invention is preferably used in a formulation that comprises or contains, more preferably consists essentially of, very preferably exclusively of, a p-type (electron donor) semiconductor and an n-type (electron acceptor) semiconductor. The p-type semiconductor is constituted by a polymer according to the present invention. The n-type semiconductor can be an inorganic material such as zinc oxide or cadmium selenide, or an organic material such as a fullerene derivate, for example (6,6)-phenyl-butyric acid methyl ester derivatized methano $C_{60}$ fullerene, also known as "PCBM" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or an structural analogous compound with e.g. a $C_{70}$ fullerene group ($C_{70}$PCBM), or a polymer (see for example Coakley, K. M. and McGehee, M. D. Chem. Mater. 2004, 16, 4533).

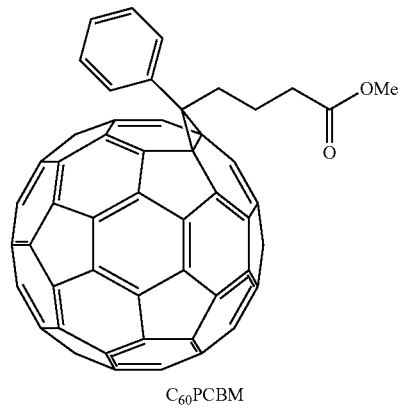

$C_{60}$PCBM

A preferred material of this type is a blend or mixture of a polymer according to the present invention with a $C_{60}$ or $C_{70}$ fullerene or modified fullerene like PCBM. Preferably the ratio polymer:fullerene is from 2:1 to 1:2 by weight, more preferably from 1.2:1 to 1:1.2 by weight, most preferably 1:1 by weight. For the blended mixture, an optional annealing step may be necessary to optimize blend morphology and consequently OPV device performance.

The OPV device can for example be of any type known from the literature [see e.g. Waldauf et al., Appl. Phys. Lett. 89, 233517 (2006)].

A first preferred OPV device according to the invention comprises:
  a low work function electrode (11) (for example a metal, such as aluminum), and a high work function electrode (12) (for example ITO), one of which is transparent,
  a layer (13) (also referred to as "active layer") comprising a hole transporting material and an electron transporting material, preferably selected from OSC materials, situated between the electrodes (11,12); the active layer can exist for example as a bilayer or two distinct layers or blend or mixture of p-type and n-type semiconductor, forming a bulk heterjunction (BHJ) (see for example Coakley, K. M. and McGehee, M. D. Chem. Mater. 2004, 16, 4533),
  an optional conducting polymer layer (14), for example comprising a blend of PEDOT:PSS (poly(3,4-ethylene-dioxythiophene): poly(styrenesulfonate)), situated between the active layer (13) and the high work function electrode (12), to modify the work function of the high work function electrode to provide an ohmic contact for holes,
  an optional coating (15) (for example of LiF) on the side of the low workfunction electrode (11) facing the active layer (13), to provide an ohmic contact for electrons.

A second preferred OPV device according to the invention is an inverted OPV device and comprises:
  a low work function electrode (21) (for example a metal, such as gold), and a high work function electrode (22) (for example ITO), one of which is transparent,
  a layer (23) (also referred to as "active layer") comprising a hole transporting material and an electron transporting material, preferably selected from OSC materials, situated between the electrodes (21,22); the active layer can exist for example as a bilayer or two distinct layers or blend or mixture of p-type and n-type semiconductor, forming a BHJ, an optional conducting polymer layer (24), for example comprising a blend of PEDOT:PSS, situated between the active layer (23) and the low work function electrode (21) to provide an ohmic contact for electrons, an optional coating (25) (for example of $TiO_x$) on the side of the high workfunction electrode (22) facing the active layer (23), to provide an ohmic contact for holes.

In the OPV devices of the present invent invention the p-type and n-type semiconductor materials are preferably selected from the materials, like the polymer/fullerene systems, as described above. If the bilayer is a blend an optional annealing step may be necessary to optimize device performance.

The compound, formulation and layer of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a polymer, polymer blend, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. No. 5,892,244, U.S. Pat. No. 5,998,804, U.S. Pat. No. 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
a source electrode,
a drain electrode,
a gate electrode,
a semiconducting layer,
one or more gate insulator layers,
optionally a substrate.
wherein the semiconductor layer preferably comprises a polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric constant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111-112, 2000, 31-34, Alcala, J. Appl. Phys., 88, 2000, 7124-7128 and the literature cited therein.

According to another use, the materials according to this invention, especially those showing photoluminescent properties, may be employed as materials of light sources, e.g. in display devices, as described in EP 0 889 350 A1 or by C. Weder et al., Science, 279, 1998, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantation of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., Cl—, Br—, I—, $HSO_4$, $SO_4^{2-}$, $NO_3^-$, $ClO_4^-$, $BF_4^-$, $PF6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3.6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention may also be suitable for use in organic plasmon-emitting diodes (OPEDs), as described for example in Koller et al., Nature Photonics 2008 (published online Sep. 28, 2008).

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, Proc. Natl. Acad. Sci. U.S.A. 1999, 96, 12287; D. Wang, X. Gong, P. S. Heeger, F. Rininsland, G. C. Bazan and A. J. Heeger, Proc. Natl. Acad. Sci. U.S.A. 2002, 99, 49; N. DiCesare, M. R. Pinot, K. S. Schanze and J. R. Lakowicz, Langmuir 2002, 18, 7785; D. T. McQuade, A. E. Pullen, T. M. Swager, Chem. Rev. 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The invention will now be described in more detail by reference to the following examples, which are illustrative only and do not limit the scope of the invention.

Example 1

1.1 3,6-Bis-(3-octyl-thiophen-2-yl)-thieno[3,2-b]thiophene-2,5-dione

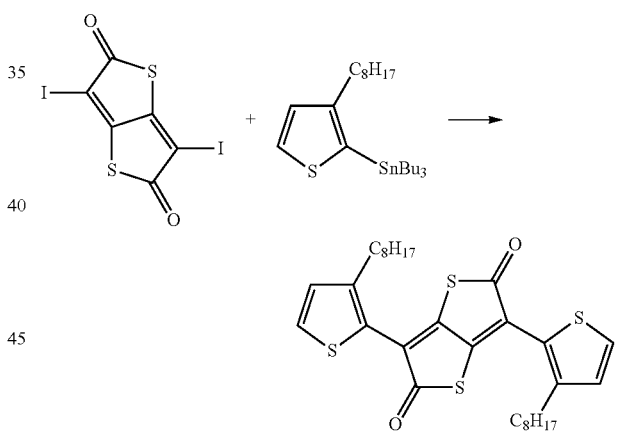

The 3,6-diiodo-thieno[3,2-b]thiophene-2,5-dione (1.000 g; 2.370 mmol), tributyl-(3-octyl-thiophen-2-yl)-stannane (Bras, Jérôme; Guillerez, Stéphane; Pépin-Donat, Brigitte. Chem. Mater. 2000, 12, 2372-2384) (2.977 g; 5.213 mmol), $PdCl_2(PPh_3)_2$ (166 mg; 0.237 mmol), copper Iodide (45 mg; 0.237 mmol) and toluene (100 cm³) is added in a 250 cm³ flask. The resulting mixture is carefully degassed for 30 minutes, and then heated at 90° C. for 16 h under nitrogen protection. Silica is added and the solvent removed in vacuo. The crude product is purified by column chromatography (eluent: petroleum ether 40-60:DCM; 70:30 ratio) to recover the pure product as a red powder (612 mg, Yield: 46%). NMR (1H, 300 MHz, $CDCl_3$): δ 7.47 (d, J=5.1 Hz, 2H); 7.02 (d, J=5.1 Hz, 2H); 2.57 (t, J=7.8 Hz, 4H); 1.61 (m, 4H); 1.26 (m, 20H); 0.86 (t, J=6.7 Hz, 6H). NMR ($^{13}C$, 75 MHz, $CDCl_3$): δ 186.92; 154.77; 145.82; 129.91; 192.26; 129.05; 123.79; 32.01; 30.70; 30.06; 29.61; 29.52; 29.37; 22.81; 14.27.

1.2 3,6-Bis-(5-bromo-3-octyl-thiophen-2-yl)-thieno[3,2-b]thiophene-2,5-dione

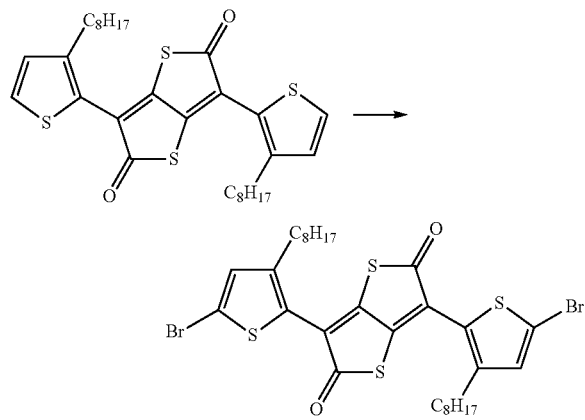

The 3,6-bis-(3-octyl-thiophen-2-yl)-thieno[3,2-b]thiophene-2,5-dione (1.1) (418 mg; 0.748 mmol) is dissolved in anhydrous DMF (7.5 cm³) at 60° C. before adding under the protection of inert atmosphere and light, the 1-Bromo-pyrrolidine-2,5-dione (NBS) (253 mg; 1.421 mmol) slowly in one portion. After 24 hours, the reaction mixture is poured in a 5% aqueous solution of sodium thiosulfate. The aqueous layer is extracted with DCM (3×100 cm³) and the combined organic fraction dried over magnesium sulfate and removed in vacuo. The crude product is purified several times by column chromatography (eluent: petroleum ether 40-60:DCM; 70:30 ratio) to recover the pure product as a red powder (205 mg, Yield: 38%). NMR ($^1$H, 300 MHz, CDCl$_3$): δ 6.99 (s, 2H); 2.50 (t, J=7.8 Hz, 4H); 1.57 (m, 6H); 1.21 (m, 18H); 0.86 (t, J=6.7 Hz, 6H). NMR ($^{13}$C, 75 MHz, CDCl$_3$): δ 186.29; 154.78; 146.57; 132.64; 128.15; 125.13; 116.75; 31.98; 30.52; 30.25; 29.52; 29.47; 29.33; 22.81; 14.27

1.3 Poly(2,6-[4,8-didodecyl-benzo{1,2-b;4,5-b'}dithiophene]-alt-[5,5'-(3,6-bis-{3-octyl-thiophen-2-yl}-thieno{3,2-b}thiophene-2,5-dione)])

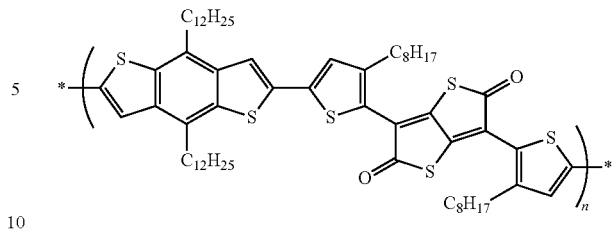

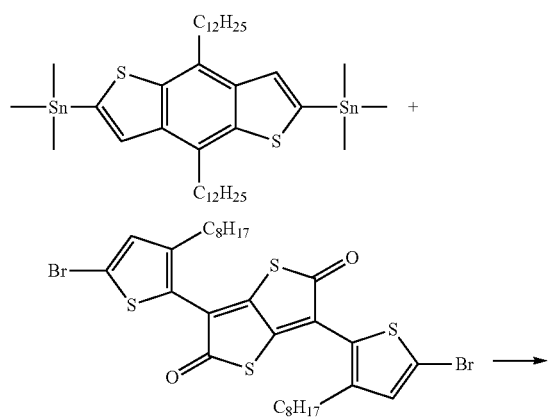

In a microwave tube, 4,8-didodecyl-2,6-bis-trimethylstannanyl-benzo[1,2-b;4,5-b']dithiophene (237.9 mg; 0.279 mmol), 3,6-Bis-(5-bromo-3-octyl-thiophen-2-yl)-thieno[3,2-b]thiophene-2,5-dione (200.0 mg; 0.279 mmol), Pd$_2$dba$_3$ (2.6 mg; 0.003 mmol) and tri-o-tolyl-phosphine (3.4 mg; 0.011 mmol) are dissolved in degassed toluene (8.0 cm³) and degassed DMF (2.0 cm³). The reaction mixture is further degassed for 30 minutes and the reaction mixture heated over microwave (Initiator, Biotage AB) at 180° C. for 20 minutes. The polymer is purified by precipitation into methanol (150 cm³), filtered and washed sequentially via Soxhlet extraction with acetone, petroleum ether 40-60, chloroform and chlorobenzene. The chlorobenzene fraction is reduced to a smaller volume in vacuo and precipitated into methanol (200 cm³). The precipitated polymer is filtered and dried under vacuum at 25° C. overnight to afford the product (188 mg, yield 62%). GPC (140° C., 1,2,4-trichlorobenzene) M$_n$: 68.4 kg·mol$^{-1}$, Mw: 185.9 kg·mol$^{-1}$, PDI: 2.71

1.4 Transistor Fabrication and Measurement

Top-gate thin-film organic field-effect transistors (OFETs) are fabricated on glass substrates with photolithographically defined Au source-drain electrodes. Thin semiconductor films are then deposited by spin-coating a solution of polymer (1.3) in o-dichlorobenzene (7 mg cm$^{-3}$) onto the substrate. The sample is then dried and annealed at 100° C. under nitrogen for 10 minutes. Next a fluoropolymer dielectric material (Lisicon® D139 from Merck KGaA) is spin-coated ontop. Finally a photolithographically defined Au gate electrode is deposited. The electrical characterization of the transistor devices is carried out in ambient air atmosphere using computer controlled Agilent 4155C Semiconductor Parameter Analyser. Field-effect mobility is calculated in the saturation regime ($V_d$>($V_g$-$V_0$)) using equation (1):

$$\left(\frac{dI_d^{sat}}{dV_g}\right)_{V_d} = \frac{WC_i}{L}\mu^{sat}(V_g - V_0) \quad (1)$$

where W is the channel width, L the channel length, C$_i$ the capacitance of insulating layer, V$_g$ the gate voltage, V$_0$ the turn-on voltage, and μ$_{sat}$ is the charge carrier mobility in the saturation regime. Turn-on voltage (V$_0$) is determined as the onset of source-drain current.

For polymer (1.3), field-effect mobility in the saturation regime (μ$_{sat}$) of 7×10$^{-3}$ cm$^2$·V$^{-1}$·s$^{-1}$ is calculated and a current on/off ratio of 1×10$^4$ is observed.

FIG. 1 shows the current-voltage characteristic (A), linear mobility (B) and saturated mobility (C) for an OFET with polymer 1.3.

The invention claimed is:

1. A polymer comprising one or more units of formula I

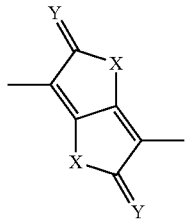   I wherein X and Y are independently of each other S or O.

2. A polymer according to claim 1, wherein the units of formula I are selected from formulae Ia-Id:

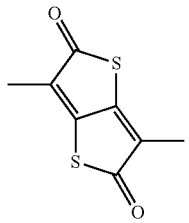   Ia

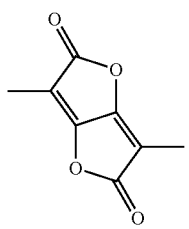   Ib

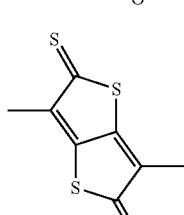   Ic

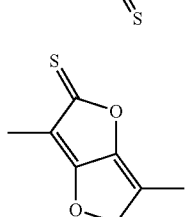   Id

3. A polymer according to claim 1, wherein said polymer contains one or more units of formula I1

   I1 wherein

U is a unit of formula I as defined in claim 1 or is a unit of formula Ia-Id,

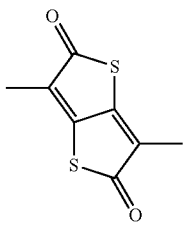   Ia

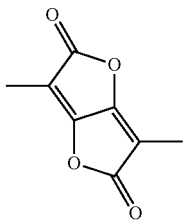   Ib

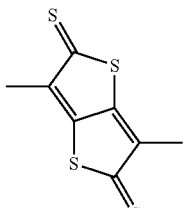   Ic

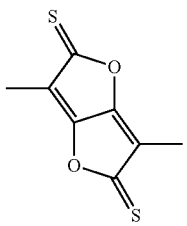   Id $Ar^1$, $Ar^2$, $Ar^3$ are, on each occurrence identically or differently, and independently of each other, aryl or heteroaryl having 5 to 30 ring atoms, which is optionally substituted, and a, b, c, d are on each occurrence identically or differently 0, 1 or 2, wherein in at least one repeating unit b is 1.

4. A polymer according to claim 3, wherein said polymer contains one or more additional repeating units selected of formula II

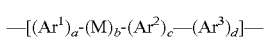   II wherein $Ar^1$, $Ar^2$, $Ar^3$, a, b, c and d are as defined in claim 3, and M is an aryl or heteroaryl group having 5 to 30 ring atoms which is optionally substituted.

5. A polymer according to claim 1, wherein said polymer is selected from formula III:

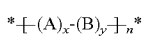   III wherein
A is a unit of formula I, Ia-Id or I1

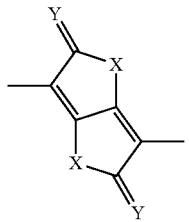 I

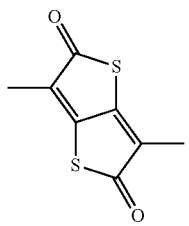 Ia

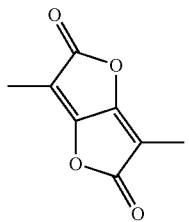 Ib

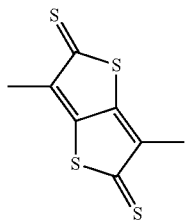 Ic

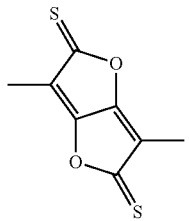 Id

—[(Ar$^1$)$_a$—(U)$_b$—(Ar$^2$)$_c$—(Ar$^3$)$_d$]— I1 wherein
U is a unit of formula I or Ia-Id,
Ar$^1$, Ar$^2$, Ar$^3$ are, on each occurrence identically or differently, and independently of each other, aryl or heteroaryl having 5 to 30 ring atoms, which is optionally substituted,
a, b, c, d are on each occurrence identically or differently 0, 1 or 2, wherein in at least one repeating unit b is 1,
B is a unit comprising one or more aryl or heteroaryl groups that are optionally substituted,
x is >0 and ≤1,
y is ≥0 and <1,
x+y is 1, and
n is an integer >1.

6. A polymer according to claim 3, wherein said polymer is selected from formula IIIa

*—[(Ar$^1$)$_a$—(U)$_b$—(Ar$^2$)$_c$—(Ar$^3$)$_d$]$_n$—* IIIa wherein U, Ar$^1$, Ar$^2$, Ar$^3$, a, b, c and d are as defined in claim 3, n is an integer >1, and wherein the individual repeating units [(Ar$^1$)$_a$—(U)$_b$—(Ar$^2$)$_c$—(Ar$^3$)$_d$] in the polymer can be identical or different from one another.

7. A polymer according to claim 3, characterized in that it is selected of formula IIIb

*—([(Ar$^1$)$_a$—(U)$_b$—(Ar$^2$)$_c$—(Ar$^3$)$_d$]$_x$——[(Ar$^1$)$_a$-(M)$_b$-(Ar$^2$)$_c$—(Ar$^3$)$_d$]$_y$)$_n$—* IIIb wherein
U, Ar$^1$, Ar$^2$, Ar$^3$, a, b, c and d are as defined in claim 3,
M is an aryl or heteroaryl group having 5 to 30 ring atoms which is optionally substituted,
x is >0 and ≤1,
y is ≥0 and <1,
x+y is 1, and
n is an integer >1.

8. A polymer according to claim 5, wherein said polymer is selected from formula IV R$^2$—[-(A)$_x$-(B)$_y$-]$_n$R$^3$ IV wherein
A, B, x, y and n are as defined in claim 5, and
R$^2$ and R$^3$ are each, independently of each other,
F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, P-Sp-, H, —CH$_2$Cl, —CHO, —CH=CH$_2$, —SiR'R"R''', —SnR'R"R''', —BR'R", —B(OR')(OR"), or —B(OH)$_2$,
R', R" and R''' are each, independently of each other, H or optionally substituted C$_{1-40}$ carbyl or hydrocarbyl, and two of R', R" and R''' may also form a ring together with the hetero atom to which they are attached,
R$^0$ and R$^{00}$ are independently of each other H or optionally substituted C$_{1-40}$ carbyl or hydrocarbyl,
P is a polymerizable or crosslinkable group,
Sp is a spacer group or a single bond, and
X$^0$ is halogen.

9. A polymer according to claim 3, wherein Ar$^1$ and Ar$^2$ are independently of each other selected from the group consisting of thiophene-2,5-diyl, thiazole-2,5-diyl, selenophene-2,5-diyl, furan-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, and selenopheno[2,3-b]thiophene-2,5-diyl, all of which are unsubstituted, or mono- or polysubstituted, and one of Ar$^1$ and Ar$^2$ may also denote a single bond.

10. A polymer according to claim 3, wherein Ar$^3$ is, on each occurrence identically or differently, selected from the group consisting of 1,4-phenylene, 2,3-dicyano-1,4-phenylene, 2,5-dicyano, 2,3-difluro-1,4-phenylene, 2,5-difluoro-1,4-phenylene, 2,3,5,6-tetrafluoro, 3,4-difluorothiophene-2,5-diyl, pyridine-2,5-diyl, pyrimidine-2,5-diyl, naphthalene-2,6-diyl, thiophene-2,5-diyl, furan-2,5-diyl, selenophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]

thiophene-2,5-diyl, selenopheno[2,3-b]thiophene-2,5-diyl, benzo[1,2-b:4,5-b']di-thiophene-2,6-diyl, benzo[2,1-b;3,4-b']dithiophene-2,7-diyl, 2,2'-dithiophene, 2,2'-diselenophene, dithieno[3,2-b:2',3'-d]silole-5,5-diyl, dithieno[3,2-b;2',3'-d]pyrrole-5,5-diyl, 4H-cyclopenta[2,1-b:3,4-b'] dithiophene-2,6-diyl, carbazole-2,7-diyl, fluorene-2,7-diyl, indaceno[1,2-b:5,6-b']dithiophene-2,7-diyl, benzo[1",2":4,5;4",5":4',5']bis(silolo[3,2-b:3',2'-b]thiophene)-2,7-diyl, phenanthro[1,10,9,8-c,d,e,f,g]carbazole-2,7-diyl, dihydrobenzo[def]carbazole-2,7-diyl, benzo[2,1,3]thiadiazole-4,7-diyl, benzo[2,1,3]selenadiazole-4,7-diyl, benzo[2,1,3]oxadiazole-4,7-diyl, 2H-benzotriazole-4,7-diyl, quinoxaline-5,8-diyl, thieno[3,4-b]pyrazine-2,5-diyl, thieno[3,4-b]thiophene-4,6-diyl, thieno[3,4-b]thiophene-6,4-diyl, thieno[2,1,3]thiadiazole-2,5-diyl, 2,5-di-thien-2-yl-thieno[2,1,3]thiadiazole, pyrrolo[3,4-c]pyrrole-1,4-dione-3,6-diyl, [1,3]thiazolo[5,4-d][1,3]thiazole-2,5-diyl or 2,5-di-thien-2-yl-[1,3]thiazolo[5,4-d][1,3]thiazole, thieno[3,4-c]pyrrole-4,6-dione-1,3-diyl, 4-oxa-1,8-dithia-as-indacene-2,7-diyl, and benzo[c]chromene-3,8-diyl, all of which are unsubstituted, or mono- or polysubstituted.

11. A polymer according to claim 4, wherein M is, on each occurrence identically or differently, selected from the group consisting of 1,4-phenylene, 2,3-dicyano-1,4-phenylene, 2,5-dicyano, 2,3-difluoro-1,4-phenylene, 2,5-difluoro-1,4-phenylene, 2,3,5,6-tetrafluoro, 3,4-difluorothiophene-2,5-diyl, pyridine-2,5-diyl, pyrimidine-2,5-diyl, naphthalene-2,6-diyl, thiophene-2,5-diyl, furan-2,5-diyl, selenophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, benzo[1,2-b:4,5-b']di-thiophene-2,6-diyl, benzo[2,1-b;3,4-b']dithiophene-2,7-diyl, 2,2'-dithiophene, 2,2'-diselenophene, dithieno[3,2-b:2',3'-d]silole-5,5-diyl, dithieno[3,2-b;2',3'-d]pyrrole-5,5-diyl, 4H-cyclopenta[2,1-b:3,4-b'] dithiophene-2,6-diyl, carbazole-2,7-diyl, fluorene-2,7-diyl, indaceno[1,2-b:5,6-b']dithiophene-2,7-diyl, benzo[1",2":4,5;4",5":4',5']bis(silolo[3,2-b:3',2'-b]thiophene)-2,7-diyl, phenanthro[1,10,9,8-c,d,e,f,g]carbazole-2,7-diyl, dihydrobenzo[def]carbazole-2,7-diyl, benzo[2,1,3]thiadiazole-4,7-diyl, benzo[2,1,3]selenadiazole-4,7-diyl, benzo[2,1,3]oxadiazole-4,7-diyl, 2H-benzotriazole-4,7-diyl, quinoxaline-5,8-diyl, thieno[3,4-b]pyrazine-2,5-diyl, thieno[3,4-b]thiophene-4,6-diyl, thieno[3,4-b]thiophene-6,4-diyl, thieno[2,1,3]thiadiazole-2,5-diyl, 2,5-di-thien-2-yl-thieno[2,1,3]thiadiazole, pyrrolo[3,4-c]pyrrole-1,4-dione-3,6-diyl, [1,3]thiazolo[5,4-d][1,3]thiazole-2,5-diyl or 2,5-di-thien-2-yl-[1,3]thiazolo[5,4-d][1,3]thiazole, thieno[3,4-c]pyrrole-4,6-dione-1,3-diyl, 4-oxa-1,8-dithia-as-indacene-2,7-diyl, and benzo[c]chromene-3,8-diyl, all of which are unsubstituted, or mono- or polysubstituted.

12. A polymer according to claim 3, wherein
$Ar^1$, $Ar^2$, and $Ar^3$ are in each case unsubstituted or substituted, by one or more groups $R^1$, and
$R^1$ is selected from the group consisting of primary alkyl or alkoxy with 1 to 30 C atoms, secondary alkyl or alkoxy with 3 to 30 C atoms, and tertiary alkyl or alkoxy with 4 to 30 C atoms, wherein in all these groups one or more H atoms are optionally replaced by F, or $R^1$ is selected from the group consisting of aryl, aryloxy, heteroaryl and heteroaryloxy that is optionally alkylated or alkoxylated and has 4 to 30 ring atoms.

13. A polymer according to claim 1, wherein said polymer is selected from the following subformulae

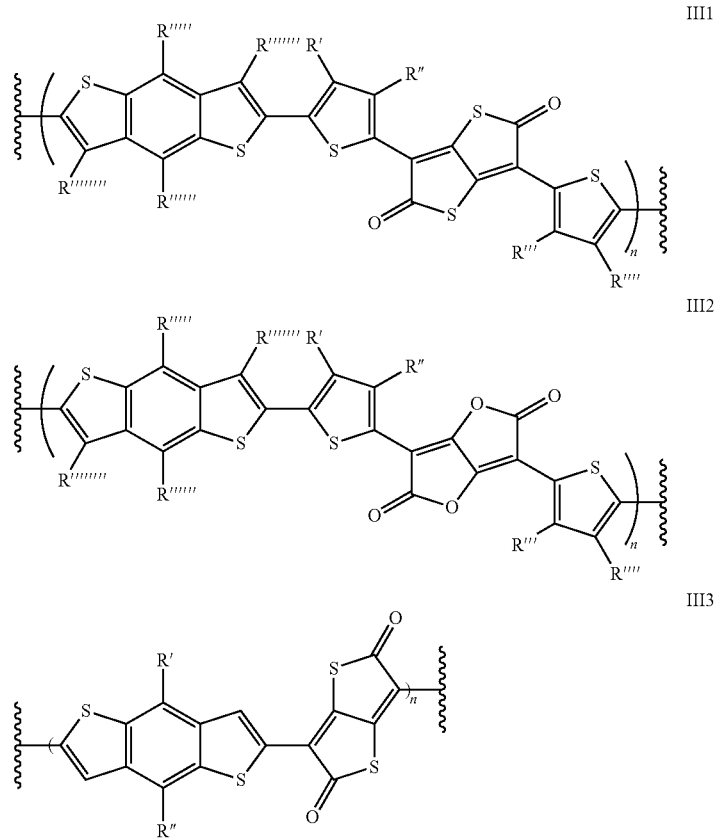

-continued
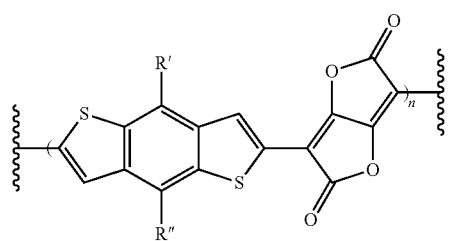
III4
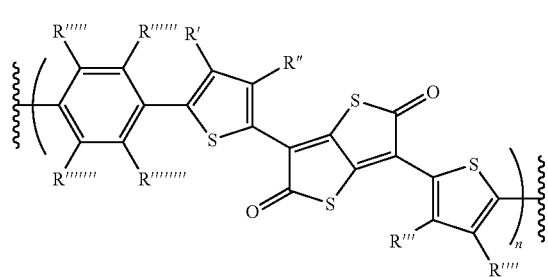
III5
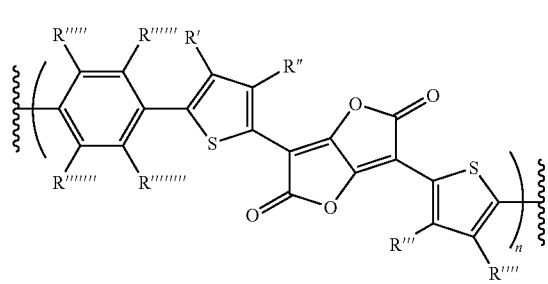
III6
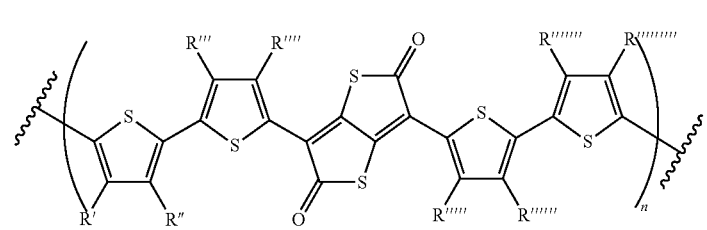
III7
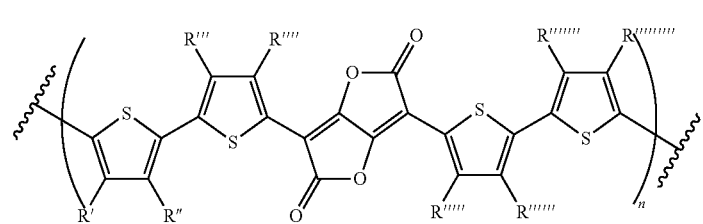
III8
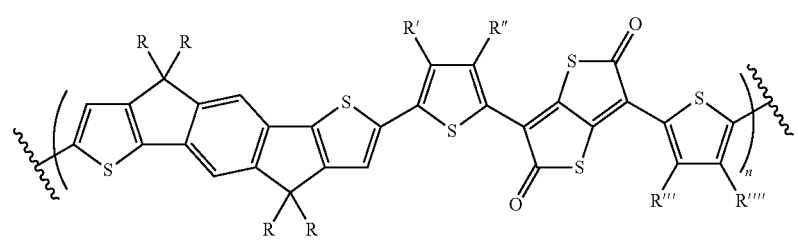
III9

-continued
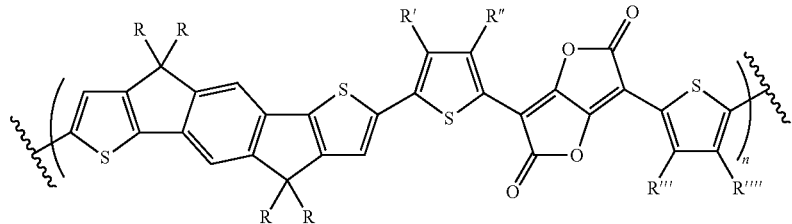
III10
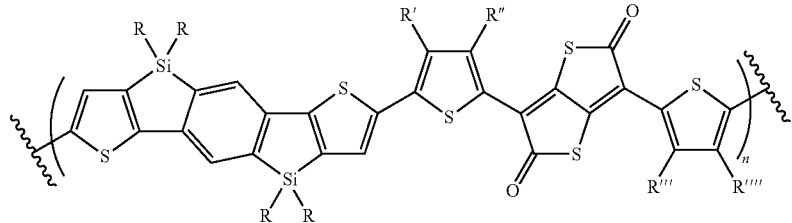
III11
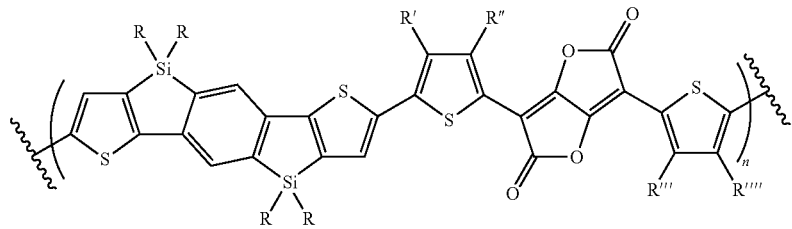
III12
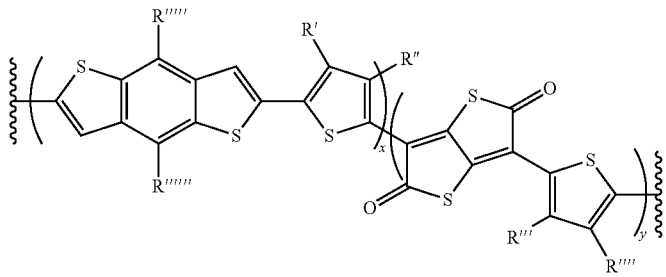
III13
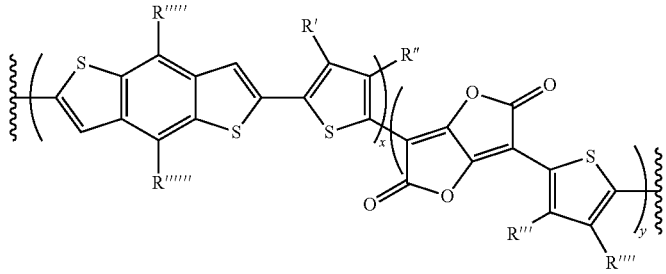
III14
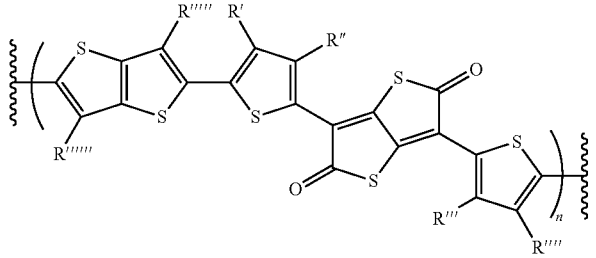
III15

-continued
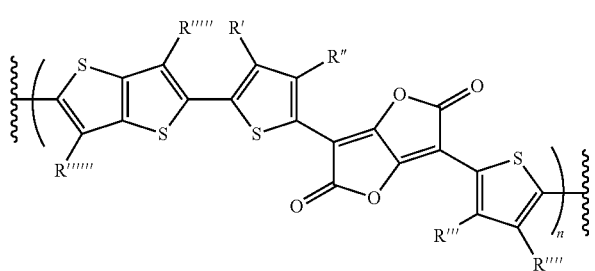
III16
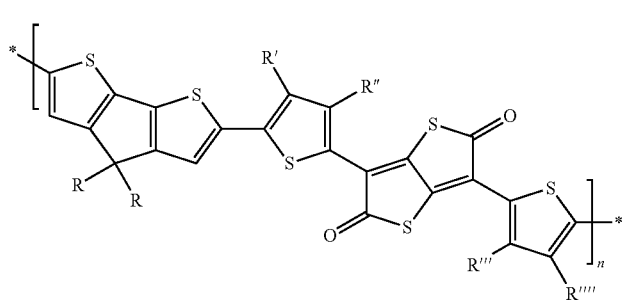
III17
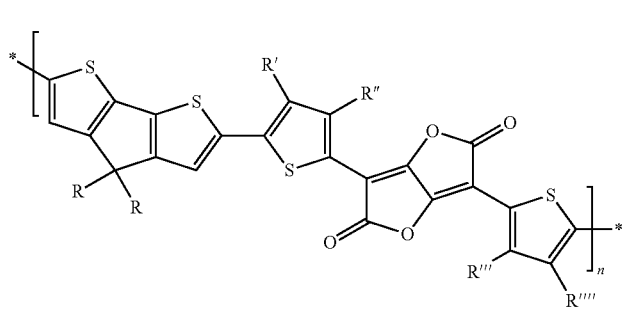
III18
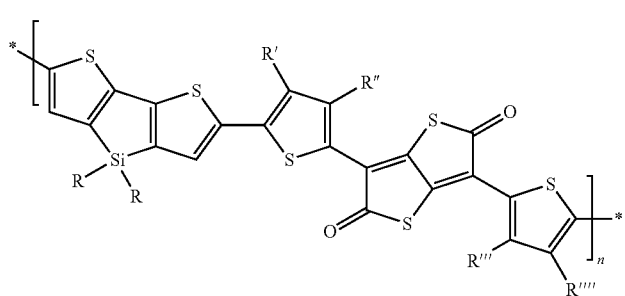
III19
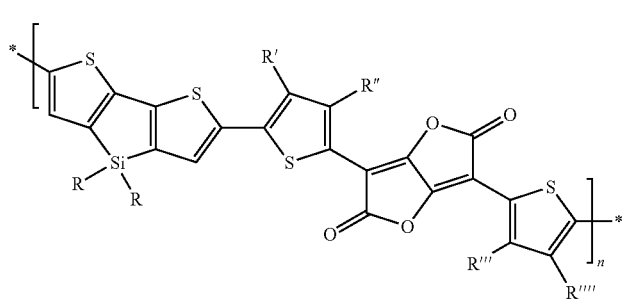
III20

-continued
III21
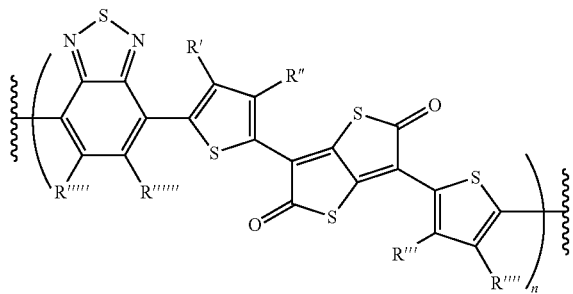
III22
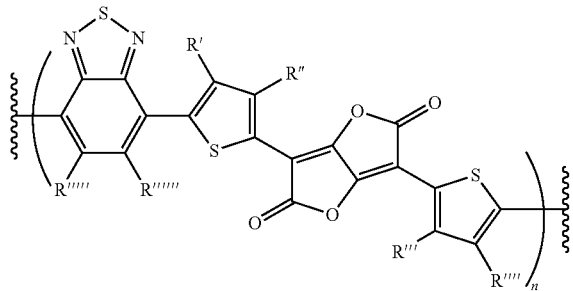
III23
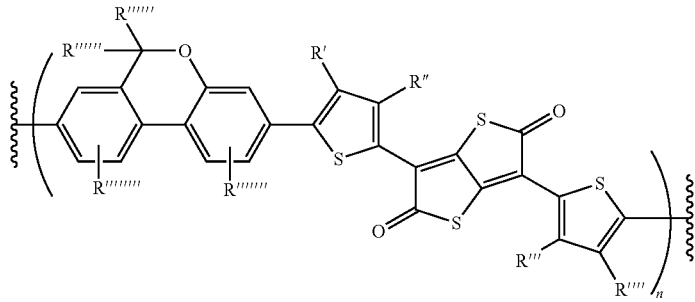
III24
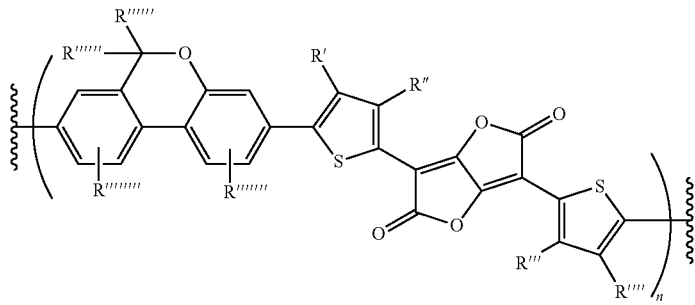
III25
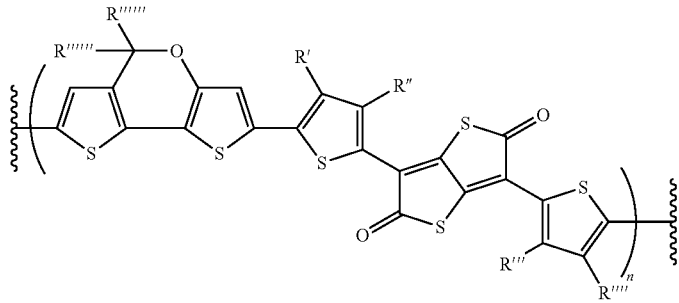

-continued

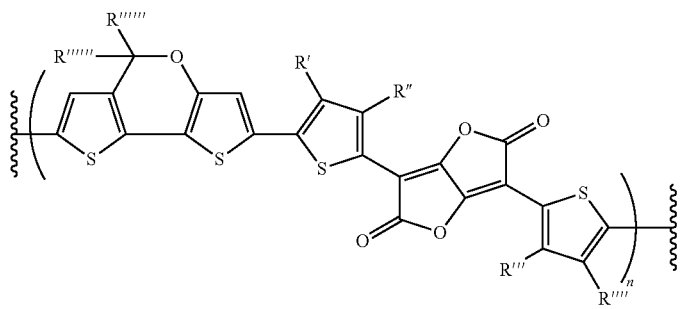

III26 wherein
x is >0 and ≤1,
y is ≥0 and <1,
x+y is 1,
n is an integer >1, and
R, R', R'', R''', R'''', R''''', R'''''' and R''''''' are on each occurrence identically or differently H, F, Br, Cl, —CN, —NC, —NCO, —NCS, —OCN, —SCN, —C(O)NR°R°°, —C(O)X°, —C(O)R°, —NH$_2$, —NR°R°°, —SH, —SR°, —SO$_3$H, —SO$_2$R°, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-.

14. A mixture or blend comprising one or more polymers according to claim 1 and one or more compounds or polymers having semiconducting, charge transport, hole/electron transport, hole/electron blocking, electrically conducting, photoconducting or light emitting properties.

15. A formulation comprising one or more polymers according to claim 1, and one or more solvents, preferably selected from organic solvents.

16. An optical, electrooptical, electronic, electroluminescent or photoluminescent component or device containing a polymer according to claim 1 as charge transport, semiconducting, electrically conducting, photoconducting or light emitting material.

17. An optical, electrooptical or electronic component or device comprising a mixture or blend according to claim 14.

18. A component or device according to claim 17, which is selected from the group consisting of organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

19. A component or device according to claim 17, which is an OFET or a bulk heterojunction OPV device.

20. A process of preparing a polymer comprising: coupling one or more monomers according to formula V

wherein
U is a unit of formula I or a unit of formula Ia-Id,

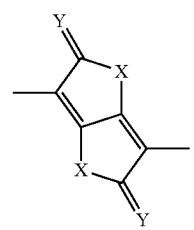

I

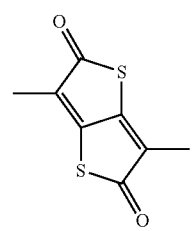

Ia

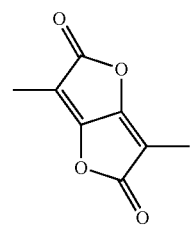

Ib

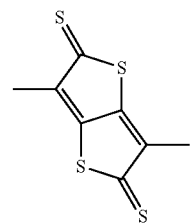

Ic

-continued

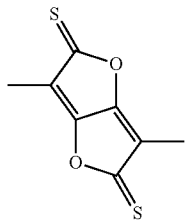
Id

R² and R³ are each, independently of each other, F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H—SO₂R⁰, —OH, —NO₂—CF₃, —SF₅, optionally substituted silyl, carbyl or hydrocarbyl with 1 to 40 C atoms that is optionally substituted and optionally comprises one or more hetero atoms, P-Sp-, H, —CH₂Cl, —CHO, —CH=CH₂, —SiR'R"R'", —SnR'R"R'", —BR'R", —B(OR')(OR"), or —B(OH)₂, R⁰ and R⁰⁰ are independently of each other H or optionally substituted C₁₋₄₀ carbyl or hydrocarbyl, P is a polymerizable or crosslinkable group, Sp is a spacer group or a single bond, X⁰ is halogen, R', R" and R'" are each, independently of each other, H or optionally substituted C₁₋₄₀ carbyl or hydrocarbyl, and two of R', R" and R'" may also form a ring together with the hetero atom to which they are attached, Ar¹, Ar² are, on each occurrence identically or differently, and independently of each other, aryl or heteroaryl having 5 to 30 ring atoms, which is optionally substituted, with each other, and/or with one or more monomers of the formula R²—Ar³—R³ wherein Ar³, R² and R³ are as defined
in an aryl-aryl coupling reaction.

21. A polymer according to claim 3, wherein
Ar¹, Ar², and Ar³ are in each case unsubstituted or substituted by one or more groups R¹,
R¹ is on each occurrence identically or differently F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms, or P-Sp-,
R⁰ and R⁰⁰ are independently of each other H or optionally substituted C₁₋₄₀ carbyl or hydrocarbyl,
P is a polymerizable or crosslinkable group,
Sp is a spacer group or a single bond, and
X⁰ is halogen.

22. A polymer according to claim 21, wherein said polymer contains one or more additional repeating units selected of formula II —[(Ar¹)ₐ-(M)ᵦ-(Ar²)ᶜ—(Ar³)ᵈ]—     II wherein Ar¹, Ar², Ar³, a, b, c and d are as defined in claim 21, and M is an aryl or heteroaryl group having 5 to 30 ring atoms which is unsubstituted or substituted by one or more groups R¹ as defined in claim 21.

23. A polymer according to claim 5, wherein said polymer B is a unit selected from formula II —[(Ar¹)ₐ-(M)ᵦ-(Ar²)ᶜ—(Ar³)ᵈ]—     II wherein Ar¹, Ar², Ar³, a, b, c and d are as defined in claim 5, and M is an aryl or heteroaryl group having 5 to 30 ring atoms which is optionally substituted.

24. A polymer according to claim 23, wherein
Ar¹, Ar², and Ar³ are in each case unsubstituted or substituted by one or more groups R¹,
M is in each case unsubstituted or substituted by one or more groups R¹,
R¹ is on each occurrence identically or differently F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms, or P-Sp-,
R⁰ and R⁰⁰ are independently of each other H or optionally substituted C₁₋₄₀ carbyl or hydrocarbyl,
P is a polymerizable or crosslinkable group,
Sp is a spacer group or a single bond, and
X⁰ is halogen.

25. A polymer according to claim 5, wherein
Ar¹, Ar², and Ar³ are in each case unsubstituted or substituted by one or more groups R¹,
R¹ is on each occurrence identically or differently F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms, or P-Sp-,
R⁰ and R⁰⁰ are independently of each other H or optionally substituted C₁₋₄₀ carbyl or hydrocarbyl,
P is a polymerizable or crosslinkable group,
Sp is a spacer group or a single bond, and
X⁰ is halogen.

26. A polymer according to claim 6, wherein
Ar¹, Ar², and Ar³ are in each case unsubstituted or substituted by one or more groups R¹,
R¹ is on each occurrence identically or differently F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms, or P-Sp-,
R⁰ and R⁰⁰ are independently of each other H or optionally substituted C₁₋₄₀ carbyl or hydrocarbyl,
P is a polymerizable or crosslinkable group,
Sp is a spacer group or a single bond, and
X⁰ is halogen.

27. A polymer according to claim 7, wherein
Ar¹, Ar², and Ar³ are in each case unsubstituted or substituted by one or more groups R¹,
M is in each case unsubstituted or substituted by one or more groups R¹,
R¹ is on each occurrence identically or differently F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms, or P-Sp-, $R^0$ and $R^{00}$ are independently of each other H or optionally substituted $C_{1-40}$ carbyl or hydrocarbyl, P is a polymerizable or crosslinkable group, Sp is a spacer group or a single bond, and $X^0$ is halogen.

28. A polymer according to claim 9, wherein $Ar^1$, $Ar^2$, and $Ar^3$ are in each case unsubstituted or substituted by one or more groups $R^1$, $R^1$ is on each occurrence identically or differently F, Br, Cl, —CN, —NC, —NCO, —NCS, —OCN, —SCN, —C(O)$NR^0R^{00}$, —C(O)$X^0$, —C(O)$R^0$, —$NH_2$, —$NR^0R^{00}$, —SH, —$SR^0$, —$SO_3H$, —$SO_2R^0$, —OH, —$NO_2$, —$CF_3$, —$SF_5$, optionally substituted silyl, carbyl or hydrocarbyl with 1 to 40 C atoms that is optionally substituted and optionally comprises one or more hetero atoms, or P-Sp-, $R^0$ and $R^{00}$ are independently of each other H or optionally substituted $C_{1-40}$ carbyl or hydrocarbyl, P is a polymerizable or crosslinkable group, Sp is a spacer group or a single bond, and $X^0$ is halogen.

29. A polymer according to claim 10, wherein $Ar^1$, $Ar^2$, and $Ar^3$ are in each case unsubstituted or substituted by one or more groups $R^1$, $R^1$ is on each occurrence identically or differently F, Br, Cl, —CN, —NC, —NCO, —NCS, —OCN, —SCN, —C(O)$NR^0R^{00}$, —C(O)$X^0$, —C(O)$R^0$, —$NH_2$, —$NR^0R^{00}$, —SH, —$SR^0$, —$SO_3H$, —$SO_2R^0$, —OH, —$NO_2$, —$CF_3$, —$SF_5$, optionally substituted silyl, carbyl or hydrocarbyl with 1 to 40 C atoms that is optionally substituted and optionally comprises one or more hetero atoms, or P-Sp-, $R^0$ and $R^{00}$ are independently of each other H or optionally substituted $C_{1-40}$ carbyl or hydrocarbyl, P is a polymerizable or crosslinkable group, Sp is a spacer group or a single bond, and $X^0$ is halogen.

30. A polymer according to claim 11, wherein $Ar^1$, $Ar^2$, and $Ar^3$ are in each case unsubstituted or substituted by one or more groups $R^1$, M is in each case unsubstituted or substituted, by one or more groups $R^1$, $R^1$ is on each occurrence identically or differently F, Br, Cl, —CN, —NC, —NCO, —NCS, —OCN, —SCN, —C(O)$NR^0R^{00}$, —C(O)$X^0$, —C(O)$R^0$, —$NH_2$, —$NR^0R^{00}$, —SH, —$SR^0$, —$SO_3H$, —$SO_2R^0$, —OH, —$NO_2$, —$CF_3$, —$SF_5$, optionally substituted silyl, carbyl or hydrocarbyl with 1 to 40 C atoms that is optionally substituted and optionally comprises one or more hetero atoms, or P-Sp-, $R^0$ and $R^{00}$ are independently of each other H or optionally substituted $C_{1-40}$ carbyl or hydrocarbyl, P is a polymerizable or crosslinkable group, Sp is a spacer group or a single bond, and $X^0$ is halogen.

* * * * *